US008361167B2

(12) United States Patent
Blackburn et al.

(10) Patent No.: US 8,361,167 B2
(45) Date of Patent: Jan. 29, 2013

(54) NATURAL HAIR DYES

(75) Inventors: Richard Simon Blackburn, Leeds (GB); Paul Martin Rose, Leeds (GB); Christopher Mark Rayner, Leeds (GB)

(73) Assignee: University of Leeds (GB)

( * ) Notice: Subject to any disclaimer, the term of this patent is extended or adjusted under 35 U.S.C. 154(b) by 0 days.

(21) Appl. No.: 13/320,556

(22) PCT Filed: May 14, 2010

(86) PCT No.: PCT/GB2010/050790
§ 371 (c)(1),
(2), (4) Date: Nov. 15, 2011

(87) PCT Pub. No.: WO2010/131049
PCT Pub. Date: Nov. 18, 2010

(65) Prior Publication Data
US 2012/0060303 A1    Mar. 15, 2012

(30) Foreign Application Priority Data
May 15, 2009    (GB) .................................... 0908397.3

(51) Int. Cl.
*A61Q 5/10*    (2006.01)
(52) U.S. Cl. ............. 8/405; 8/424; 8/435; 8/572; 8/576; 8/646
(58) Field of Classification Search ............. 8/405, 424, 8/435, 572, 576, 646
See application file for complete search history.

(56) References Cited

U.S. PATENT DOCUMENTS
6,241,785 B1    6/2001    Darmenton et al.

2007/0166256 A1    7/2007    Shiroyama et al.
2007/0251024 A1    11/2007    Greaves et al.

FOREIGN PATENT DOCUMENTS
| DE | 102007041493 | | 3/2009 |
|----|---|---|---|
| JP | 362153211 A | * | 7/1987 |
| JP | 2001172143 | | 6/2001 |
| PL | 192692 | | 11/2006 |
| WO | WO 9911223 | | 3/1999 |
| WO | WO 2004082646 | | 9/2004 |
| WO | WO 2005107780 | | 11/2005 |
| WO | WO 2006061847 | | 6/2006 |
| WO | WO 2007007936 | | 1/2007 |
| WO | WO 2010006957 | | 1/2010 |

OTHER PUBLICATIONS

STIC Search Report dated Apr. 25, 2012.*
International Preliminary Report on Patentability issued by the International Bureau, for corresponding International Patent Application No. PCT/GB2010/050790 on May 18, 2012.

* cited by examiner

*Primary Examiner* — Eisa Elhilo
(74) *Attorney, Agent, or Firm* — Marianne Fuierer; Moore & Van Allen, PLLC

(57) ABSTRACT

The invention provides dye mixtures for application to human hair, the dye mixtures comprising polyphenolic materials, these materials being obtained from botanical sources. Preferably, the botanical source is fruit, especially fruit selected from blackcurrants, blackberries, blueberries, bilberries, cranberries, grapes, chokeberries, Saskatoon berries, seabuckthorn, mulberries acai, cherries, red cabbage and/or figs. Preferably, the polyphenolic materials comprise anthocyanin compounds which, most preferably, are aglycone anthocyanidins or glycosylated anthocyanins of the formula (III):

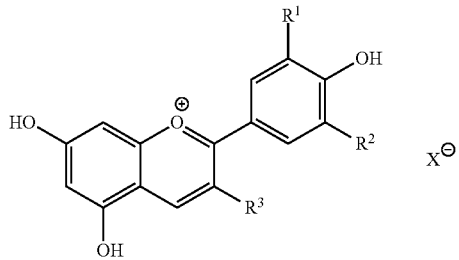 (III)
wherein $R^1$ and $R^2$ are, independently, H, OH or $OCH_3$, $R^3$ is OH (aglycone anthocyanidins) or a glycosyl group (glycosylated anthocyanins), and x is a counter-ion. The invention also provides methods for the preparation of these dye mixtures and for the use of the dye mixtures in the semi-permanent coloration of human hair.
33 Claims, 15 Drawing Sheets

NATURAL HAIR DYES

CROSS-REFERENCE TO RELATED APPLICATIONS

This application is filed under the provisions of 35 U.S.C. §371 and claims the priority of International Patent Application No. PCT/GB2010/050790 filed on May 14, 2010, which in turn claims priority to GB 0908397.3 filed May 15, 2009.

FIELD OF THE INVENTION

The present invention is concerned with the coloration of human hair, and with the provision of dyes for such applications. More particularly, the invention relates to dyes which are obtained from natural products, and their use in such applications.

BACKGROUND TO THE INVENTION

Semi-permanent hair coloration is an increasingly significant activity on a global basis, with the numbers of people using hair colorants, both in professional salons and in their own homes, increasing at a rapid rate. However, due to the chemical nature of many hair dyes, the users of these products are exposed to significant health risks, and there would be clear benefits for those who do apply hair colorants themselves, or undergo professional hair colouring treatments, in the development of alternative natural, non-toxic, non-carcinogenic products and application methods, which would minimise any potential hazards to human health.

Many commercial hair dyes are synthetically derived from petroleum feedstocks, and their manufacture frequently involves handling hazardous intermediates and the consumption of large volumes of petroleum based solvents. Furthermore, present hair coloration techniques typically involve the waste of up to 95% of the colour applied, which thereby is discharged to watercourses. Clearly, therefore, there would be considerable benefit in the development of biodegradable colorants, extracted from natural sources, and involving the use of benign technologies.

There has previously been interest in various colorants which occur in natural products, and one class that has received some attention is the group of polyphenols known as anthocyanins. Various prior art documents are available which teach the use of these materials in cosmetic products.

Thus, for example, PL-B-192692 teaches a method of obtaining anthocyanin dyes, and recovering the dyes from plant production wastes. Specifically, the patent discloses the extraction of anthocyanin dyes from coloured fruits, such as blueberry, black rose and black chokeberry, and their subsequent purification and use in food, cosmetic and pharmaceutical products. A specific method for pre-treatment of the fruit, and its extraction and subsequent purification by adsorption/desorption is provided. However, the authors offer no specific mention of other fruit sources, and neither is there any reference to the use of the product, or of any related formulation.

The website of a US cosmetic producer/supplier, Act by Nature LLC (http://actbynature.com/), advertises a variety of all-natural hair colorants, including "revolutionary patent pending natural permanent hair colour, colouring tints, and colour enhancing solutions made using 100% plant derived dyes". However, limited technical information is provided regarding the nature of these dyes, although a general list of ingredients for hair dye formulations is available, and this list includes anthocyanins amongst the key ingredients. However, no further information is provided.

US-A-2006/246025 relates to natural fast-drying hair fixative compositions comprising polysaccharides, but is principally concerned with polysaccharide-based delivery systems comprising a combination of a linear polysaccharide such as pullulan and a monohydric alcohol, and includes no reference to any colouring system.

JP-A-62153211 is concerned with the use of anthocyanins in hair care products, and discloses hair preparations containing anthocyanins for dandruff control. However, it appears that the action of the disclosed anthocyanin ingredients is specifically in the control of dandruff in the disclosed hair tonics, since no mention is made of dyeing activity. Specific anthocyanin structures (I) are disclosed, although the document is silent regarding source fruit and methods of extraction and purification.

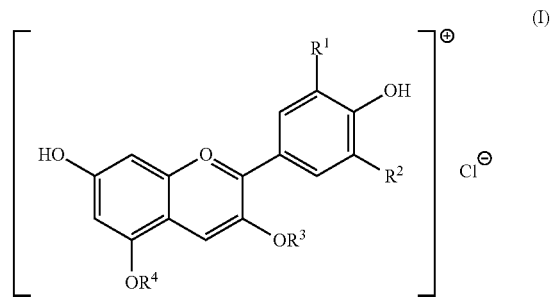

(I)

The disclosed hair preparations for control of dandruff contain at least one compound selected from anthocyanins (I) (wherein $R^1$ and $R^2$ are independently H, OH, or MeO; $R^3$ and $R^4$ are independently H or β-glucoside). Polyoxyethylene oleyl alcohol ether, delphinidin and a fragrance are added to ethanol and the alcoholic phase is added to water containing glycerine to give a hair tonic.

U.S. Pat. No. 6,620,410 teaches hair care compositions which are designed to provide increased protection from ultraviolet radiation. The disclosed formulations comprise grape skin extract, and are alleged to display anti-UV radiation properties. It is believed that the grape skin extract will inevitably contain anthocyanins, although the document contains no specific disclosure of anthocyanins, or of any other anthocyanin sources; in addition, the patent fails to teach or suggest the use of any extract for the purposes of hair coloration.

U.S. Pat. No. 6,241,785 relates to flavyllium-type compounds and their use in dyeing keratinous fibres, with particular emphasis on human hair. These derivatives are members of a chemical class to which anthocyanins belong. However, the disclosed compounds are obtained synthetically, and not via the extraction of fruit. Furthermore, the patent specifies compounds (II) having particular substitution patterns, thereby excluding anthocyanins.

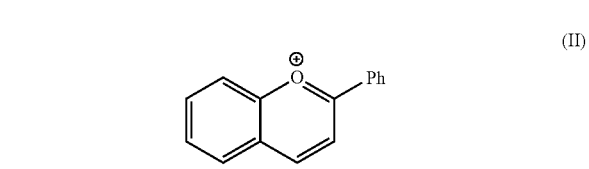 [SMILES: c1ccc(-c2ccc3ccccc3[o+]2)cc1]

(II)

JP-A-4119179 teaches a specific anthocyanin compound—cyanidin 3-O-arabinoside—for use in dyeing wool in combination with quercetin glucouronide. However, whilst the document teaches formulation of the dye, no information is provided with regard to the source of the anthocyanin, or its recovery. Furthermore, the patent concerns the dyeing of a fibre, with specific mention being made of silk and wool, and requires dyeing conditions of pH≦2.5 combined with a temperature 95° C. for 1 hour, conditions which would be wholly inappropriate for dyeing human hair. Despite its proposed use as a dye, the document makes no mention of the application of the material to hair, or indeed its use in any cosmetic application.

US-A-2007/0251024 teaches the application of natural colorants to hair in a process requiring the inclusion of a mordanting agent, such as a mineral or metal salt, in the hair dyeing process. The inventors describe the inclusion of the mordant to provide substantivity between the dye and hair fibre, inferring that in the absence of the mordant dyeing would not be possible as the limited affinity of the dyes would not allow sufficient build-up of colour on the hair fibre. The claimed invention is, in many ways, analogous to centuries-old wool dyeing processes which require application of natural dyes with a mordant. However, the document contains no suggestion of the application of natural polyphenols as dyes without a mordant.

The literature provides few examples relating to the dyeing of textile fibres with anthocyanin based dyes, although there have been recent reports of the successful application of an aqueous extract of grape pomace to dye cotton pre-mordanted with tannins, and bleached wool yarn, in each case yielding red/violet shades. The dyeings in this study were conducted by exhaustion methods, employing aqueous dyebaths with or without metal salt (or tannin) mordant added to the solution.

The increasing demand for dyes for use in the dyeing of human hair which are free from potential health hazards has presented an opportunity for manufacturers to exploit dyes such as anthocyanins, which are available from natural sources via clean technologies, for such purposes. However, there is at present no satisfactory commercial process for the production of dyes in this way. The present inventors have, therefore, investigated the production of colorants from natural sources, and have developed a range of natural compounds, and methods for their production, which facilitate the production of safe, commercially viable, hair dyes.

SUMMARY OF THE INVENTION

The present invention is concerned with the extraction and selective purification of specific polyphenolic materials from particular botanical sources, notably blackcurrant (Ribes nigrum), blackberry (Rubus), blueberry, bilberry, cranberry (Vaccinium), grape (Vitis), chokeberry (Aronia), Saskatoon berry (Amelanchier alnifolia), sea-buckthorn (Hippophae rhamnoides), mulberry (Moms), acai (Euterpe), cherry (Prunus), red cabbage (Brassica oleracea) and fig (Ficus) fruits or pressed juices, and their application within formulations as semi-permanent dyes for human hair.

Thus, according to a first aspect of the present invention, there is provided a dye mixture for application to human hair, wherein said mixture comprises a multiplicity of polyphenolic materials, wherein said materials are obtained from a botanical source.

Preferably, said botanical source is fruit. More preferably, said fruit is selected from blackcurrants, blackberries, blueberries, bilberries, cranberries, grapes, chokeberries, Saskatoon berries, sea-buckthorn, mulberries acai, cherries and/or figs.

Preferably, said polyphenolic materials comprise anthocyanin compounds of the formula (III):

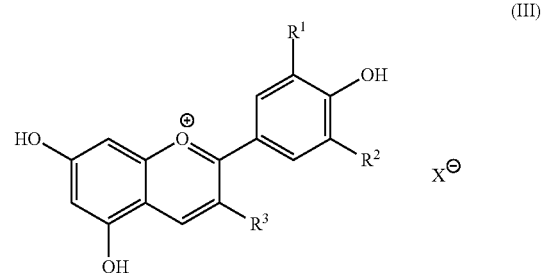

(III)

wherein $R^1$ and $R^2$ are, independently, H, OH or $OCH_3$, $R^3$ is OH (aglycone anthocyanidins) or an O-glycosyl group (glycosylated anthocyanins), and X is a counter-ion which may optionally be selected from chloride, bromide, iodide, sulphate, bisulphate, carbonate, bicarbonate, citrate, formate, acetate or tartrate.

More preferably, said anthocyanin compounds are aglycone anthocyanidins or glycosylated anthocyanins. Most preferably, said anthocyanin compounds are glycosylated anthocyanins where said glycosylation comprises a monosaccharide or disaccharide.

Specific examples of aglycone anthocyanidins include the following:

TABLE 1

Chemical composition of aglycone anthocyanidins of structure (III)

| Name | $R^1$ | $R^2$ | $R^3$ |
|---|---|---|---|
| Pelargonidin | H | H | OH |
| Cyanidin | OH | H | OH |
| Peonidin | OCH3 | H | OH |
| Delphinidin | OH | OH | OH |
| Petunidin | OH | OCH3 | OH |
| Malvinidin | OCH3 | OCH3 | OH |

Active anthocyanin compounds may comprise various O-glycosyl groups as the R3 group, for example monosaccharides or polysaccharides such as disaccharides or trisaccharides. Optionally, these glycosyl moieties may include further acyl substitution, thereby providing a multitude of naturally occurring anthocyanins Preferred monosaccharide groups include O-glucoside, O-rhamnoside, O-arabinoside, O-xyloside and O-galactoside. Preferred di- and trisaccharides are typically combinations of these monosaccharide groups, for example O-rutinoside (glucose+rhamnose), O-sophoroside (glucose+glucose) and O-primeveroside (glucose+xylose). Due to the nature of the associated bio-synthetic pathways of anthocyanin formation, particular botanical sources contain specific combinations of multiple anthocyanins. In fact, particular fruits and, indeed, varieties within species, have specific and characteristic profiles of anthocyanins, giving rise to variations in observed colour. For example, the four major anthocyanins present in blackcurrant fruit are cyanidin-3-O-glucoside, cyanidin-3-O-rutinoside, delphinidin-3-O-glucoside and delphinidin-3-O-rutinoside, and these derivatives account for >97% of the total anthocyanins in the fruit.

Once isolated, the observed colour of the anthocyanins is influenced by the chemical environment, particularly solvatochromatic effects and pH, and this allows for potential colour control in formulations incorporating these compounds.

Thus, in an especially preferred embodiment, the present invention provides highly specific mixtures of particular anthocyanins, and these mixtures are obtained by specific extraction/fractionation/purification/concentration techniques and originate from particular botanical sources. These highly specific mixtures of anthocyanins are found to adsorb onto human keratin when applied via an aqueous dye-bath, or when incorporated into a common base formulation, such as a shampoo or conditioner type base, or other base suitable for cosmetic application. The particular anthocyanins—and, indeed, the specific mixtures thereof—may be most conveniently defined in terms of their characteristic HPLC chromatographic profiles.

According to a second aspect of the present invention, there is provided a method for the preparation of the dye mixtures of the first aspect of the invention, said method comprising the extraction of said dyes from at least one botanical source and the purification of said extracted material.

Preferably, said botanical source is fruit or pressed fruit juice. More preferably, said fruit is selected from blackcurrants, blackberries, blueberries, bilberries, cranberries, grapes, chokeberries, Saskatoon berries, sea-buckthorn, mulberries, acai, cherries and/or figs.

Preferably, said dyes comprise anthocyanin compounds. Most preferably, said anthocyanin compounds comprise aglycone anthocyanidins or glycosylated anthocyanins of the formula (III) as hereinbefore defined.

According to the third aspect of the present invention, there is provided a formulation for the treatment of human hair, wherein said formulation comprises at least one dye mixture according to the first aspect of the invention.

The fourth aspect of the present invention provides for the use of the dye mixtures of the first aspect of the invention and the formulations of the third aspect of the invention for the dyeing of keratinous fibres. Preferably said keratinous fibres comprise human hair.

According to a fifth aspect of the present invention, there is provided a method for the semi-permanent coloration of human hair, said method comprising treating human hair with the dye mixtures of the first aspect of the invention or the formulations of the third aspect of the invention.

Preferably, according to the fifth aspect of the invention, the hair may be washed with water prior to said treatment with dye mixtures. Optionally, said washing procedure may also be carried out with shampoo. Optionally, said washing procedure may be followed by treatment with hair conditioner.

Several published reports have provided toxicological data relating to anthocyanins which corroborate the view that these pigments pose no threat to human health. Indeed, major driving forces for continued studies relating to these compounds are provided by the demonstrated therapeutic or medicinal properties of the materials, including antioxidative activity, anti-inflammatory activity and reduction of coronary heart disease, as well as anti-carcinogenic and anti-mutagenic properties.

These particularly positive attributes of this particular group of polyphenols makes the anthocyanin compounds especially suitable materials for inclusion in personal care products, such as hair colorants.

DESCRIPTION OF THE INVENTION

Figure 1:
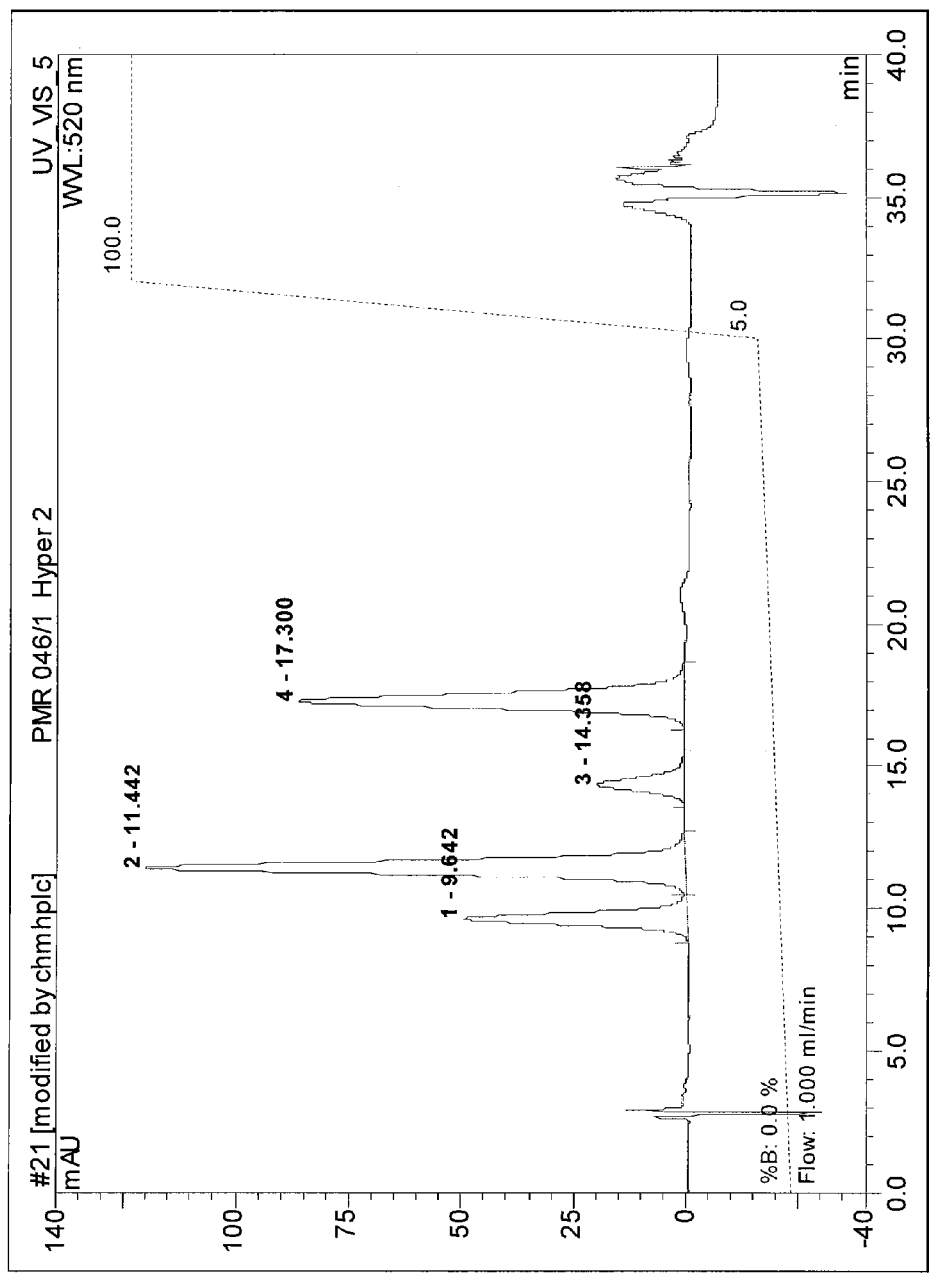
FIG. 1 shows a HPLC chromatogram of purified blackcurrant anthocyanins.

The mixtures of polyphenol derivatives according to the invention have been successfully extracted from suitable fruits or fruit juices by the present inventors, and the extracts have then been purified in order to obtain dyes suitable for application to human hair. Thus, unlike the prior art, the present invention provides for the preparation of the anthocyanin dyes from naturally available materials, i.e., fruits, wherein the dyes are in a suitable form for application as hair dyes.

Samples of dried fruit, pressed juice and fruit pomace have been successfully sourced and the inventors have been able to establish a suitable supply chain of appropriate volume and quality. Analyses of extracts from various varieties of blackcurrants, blackberries, blueberries, bilberries, chokeberries, mulberries—as well as red cabbage—were carried out, and the analytical results confirmed the anthocyanin profiles previously suggested in the literature. HPLC chromatograms were obtained which highlighted the presence and characteristic ratios of the specific anthocyanins in each source material.

The mechanism of colouration is by adsorption of the anthocyanins to hair. In order to fully investigate the type of association and interaction, thorough sorption studies have been undertaken, and the results of the associated data analysis allowed the inventors to demonstrate a Freundlich-type isotherm pattern. Further analysis of the data facilitated the optimisation of the anthocyanin profile concerning specifics of glycosylation which was found to be required for successful and controlled dyeing of hair.

Preferential adsorption was observed with certain species; for example, a purified extract profile containing anthocyanin components with the smallest possible sugar moieties attached (monosaccharides, e.g. glucoside) was found to preferentially absorb to hair when compared with anthocyanin species having larger glycosyl units (disaccharides, e.g. rutinoside).

The method of the second aspect of the invention involves the extraction of the dyes from a botanical source, and the subsequent purification of the extracted dyes. Typically, extraction is achieved by the action of aqueous media, preferably water, with or without the application of heat. Thus, if the botanical source is fruit, dyes can conveniently be extracted by heating the fruit in water. Optionally, said aqueous media may additionally comprise glycerol or ethanol and may be acidified to pH <4 by addition of any of, for example, hydrochloric, hydrobromic, hydroiodic, nitric, phosphoric, sulphuric, acetic, trifluoroacetic, ascorbic, citric, formic, lactic, tartaric, camphor-10-sulphonic or oxalic acids.

A key stage of the method is the subsequent purification process, which requires isolation of the dyes from the crude extract or fruit juice at the correct dilution. Suitable methods for achieving this include adsorption/desorption techniques using various porous solids and/or resins. Successful results were achieved with non-ionic aliphatic acrylic ester polymers, proteinaceous materials, polysaccharides, and modified variants thereof. Following removal of unwanted extraneous components, the target compounds may be eluted in an ethanolic liquid phase. Optionally, said elution media may additionally comprise glycerol or isopropyl alcohol, in conjunction with heating, typically at 20-100° C., and be mildly acidified by addition of any of, for example, hydrochloric, hydrobromic, hydroiodic, nitric, phosphoric, sulphuric, acetic, trifluoroacetic, ascorbic, citric, formic, lactic, tartaric, camphor-10-sulphonic or oxalic acids (0.01-1.0M).

The eluted solution of anthocyanins may then be powdered following removal of solvent by evaporation or by common powder forming techniques such as recrystallisation or spray drying, or by any other such technique to produce a powder. Alternatively, a concentrated liquid solution may be used for further incorporation into dye formulations.

The use of the semi-permanent dyes of the first aspect of the invention for the dyeing of keratinous fibres according to the fourth aspect of the invention, and the method of the fifth aspect of the invention for the semi-permanent coloration of human hair typically require the use of formulations of the semi-permanent dyes of the invention according to the third aspect of the invention. There are two principal considerations in this regard, the first of which is the delivery system, wherein the active dye has been successfully incorporated into base formulations suitable for cosmetic application including, but not exclusively, shampoo and conditioner type bases. Further customisation of the colorant base delivery system is possible in order to both control the stability and colour of the formulation, and maximise the amount of available active dye.

The second issue which requires consideration is the precise specification of the active dye profile, which directly affects the observed colour on hair. This is clearly affected by the botanical source material, including the particular variety that is employed, and the specific method of extraction, purification and fractionation. For example, glycosylated polyphenols are sensitive to heat and acidification resulting in hydrolysis of the glycosyl groups. Therefore, due care was taken to develop methods of isolation that preserve the glycosylation of the compounds in their natural form.

Due consideration was given to the production of mixtures of anthocyanins with different purified natural extracts in various formulations in order to create custom profiles which were demonstrated to provide a suitable range of available colours, most notably auburns and light and dark browns. Variations of such individual shades were achieved using our system by dyeing from a single formulation base containing the stabilised mixture of dye components, at room temperature, in the absence of any oxidative species, metal salts or any component acting as a mordant.

The attention of the inventors has been particularly directed towards anthocyanin dyes, and the inventors have especially studied the application of purified anthocyanins extracted from dried blackcurrant skins. The anthocyanin profile of the extract was quantitatively measured by use of a calibrated HPLC methodology and, from the acquired chromatograms, it was possible to derive precise data relating to the presence of particular anthocyanins in the dyebath.

Thus, for example, isothermic adsorption studies were conducted at room temperature (20° C.) using buffered aqueous dyebaths (pH 2.0-5.5; 0.01-0.50 M sodium citrate/citric acid) of varied anthocyanin concentration. HPLC chromatograms were recorded for samples of the dyebaths prior to, and after, dyeing of human hair. The hair samples used in the study were from bleached blonde human hair swatches, which were shampooed and rinsed prior to immersion in the dyebath.

An example dyebath chromatogram is shown in FIG. 1, with its associated data being set out in Table 1. The chromatogram clearly shows the presence of the four major anthocyanins characteristic to blackcurrant extract, these being delphinidin-3-O-glucoside (15.71%), delphinidin-3-O-rutinoside (43.25%), cyanidin-3-O-glucoside (7.03%) and cyanidin-3-O-rutinoside (34.00%) in an aqueous dye bath which had a total anthocyanin content of 256 mg dm-3.

TABLE 2

HPLC data of dye bath prior to dyeing.

| No. | Ret. Time min | Name* | Area mAU * min | Rel. Area % | Amount mg dm$^{-3}$ | Rel. Amt. Mol % |
|---|---|---|---|---|---|---|
| 1 | 9.64 | Del-3-O-Glu | 24.912 | 15.71 | 40.05 | 18.67 |
| 2 | 11.44 | Del-3-O-Rut | 68.573 | 43.25 | 110.25 | 39.81 |
| 3 | 14.36 | Cy-3-O-Glu | 11.139 | 7.03 | 19.41 | 9.38 |
| 4 | 17.30 | Cy-3-O-Rut | 53.909 | 34.00 | 86.67 | 32.14 |
| Total: | | | 158.532 | 100.00 | 256.37 | 100.00 |

*Del = delphinidin, Cy = cyanidin, Glu = glucoside, Rut = rutinoside, Rel. = Relative, Amt. = Amount Analysis of the HPLC data for the dyebath after dyeing clearly shows that all of the anthocyanins were absorbed by the hair, as the concentrations of each are seen to be reduced, as can be seen from the data in Table 2. The noted preference for anthocyanins with smaller sugar moieties attached can be seen by analysis of the exhaustion data in Table 2 (mol %).

Percentage exhaustion is a representation of how much of each constituent dye (anthocyanin) has been removed from the dyebath during the dyeing process. Due to the nature of the systems and methods used, this equates directly to the amount of dye that has been absorbed onto the fibre (keratin). As a consequence of the level of detail acquired using HPLC methodology, it is possible to determine percentage exhaustion values for individual anthocyanins, and also for the overall mixture. The higher the percentage exhaustion, the greater the amount of dye (anthocyanin) that has been removed from the dyebath.

In this example, it was noted that glucosidic (monosaccharide) anthocyanins (Del-3-O-glu and Cy-3-O-glu) were both absorbed at approximately the same exhaustion (28.74 and 29.71% respectively), whereas those with rutinoside (disaccharide) residues (Del-3-O-rut and Cy-3-O-rut) were absorbed at a greatly reduced exhaustion (12.25 and 11.64%), yet also comparable to each other.

TABLE 3

HPLC data of dye bath after dyeing of human hair.

| No. | Ret. Time (min) | Name* | Area (mAU × min) | Rel. Area (%) | Conc. (mg dm$^{-3}$) | Rel. amount (mol %) | Exhaustion (%) |
|---|---|---|---|---|---|---|---|
| 1 | 9.62 | Del-3-O-Glu | 17.752 | 13.18 | 28.54 | 13.24 | 28.74 |
| 2 | 11.51 | Del-3-O-Rut | 60.175 | 44.68 | 96.74 | 44.89 | 12.25 |
| 3 | 14.43 | Cy-3-O-Glu | 7.829 | 5.81 | 13.64 | 6.33 | 29.71 |
| 4 | 17.42 | Cy-3-O-Rut | 47.634 | 35.37 | 76.58 | 35.54 | 11.64 |
| | Total: | | 133.390 | 99.04 | 215.50 | 100.00 | 16.77 |

*Del = delphinidin, Cy = cyanidin, Glu = glucoside, Rut = rutinoside, Rel. = Relative In further experiments, successful coloration of hair was achieved using different concentrations of the same blackcurrant anthocyanin mixtures in a number of dyebath experiments, using an adsorption isotherm technique. In this way, direct, reproducible and quantifiable relationships were found to exist between pre- and post-dyebath concentrations, exhaustion and dye on fibre.

An adsorption isotherm study was performed, monitored by analysis of UV-Vis spectra of each dyebath. The parameters for the study are outlined in Table 4.

TABLE 4

Adsorption isotherm parameters

| Item | Parameter |
|---|---|
| Dye | Blackcurrant anthocyanin extract |
| Substrate | Light blonde (bleached hair) |
| Substrate quantity | 100 mg |
| Substrate pre-treatment | Shampooed |
| Solvent | 0.2M Citric acid/citrate buffer |
| Solvent volume | 5.0 ml |
| Solvent: substrate | 50:1 (volume:weight) |
| Temperature | 20° C. |
| Duration | 1 hour |
| Agitation | Stirred |

TABLE 5

Adsorption isotherm results, measured by UV-Vis absorbance.

| Entry | *omf % | $C_0$ mg dm$^{-3}$ | Exhaustion % | $C_e$ mg dm$^{-3}$ | $q_e$ mg g$^{-1}$ |
|---|---|---|---|---|---|
| 1 | 20.00 | 4000 | 25.5 | 2989.4 | 50.5 |
| 2 | 10.00 | 2000 | 17.4 | 1651.5 | 17.4 |
| 3 | 5.00 | 1000 | 23.2 | 749.1 | 12.6 |
| 4 | 2.00 | 400 | 23.6 | 291.2 | 5.4 |
| 5 | 1.00 | 200 | 25.5 | 136.1 | 3.2 |
| 6 | 0.50 | 100 | 24.2 | 67.6 | 1.6 |
| 7 | 0.20 | 40 | 30.6 | 24.1 | 0.8 |
| 8 | 0.10 | 20 | 30.6 | 11.7 | 0.4 |
| 9 | 0.05 | 10 | 44.4 | 4.5 | 0.3 |

*omf = on mass of fibre

Figure 2:
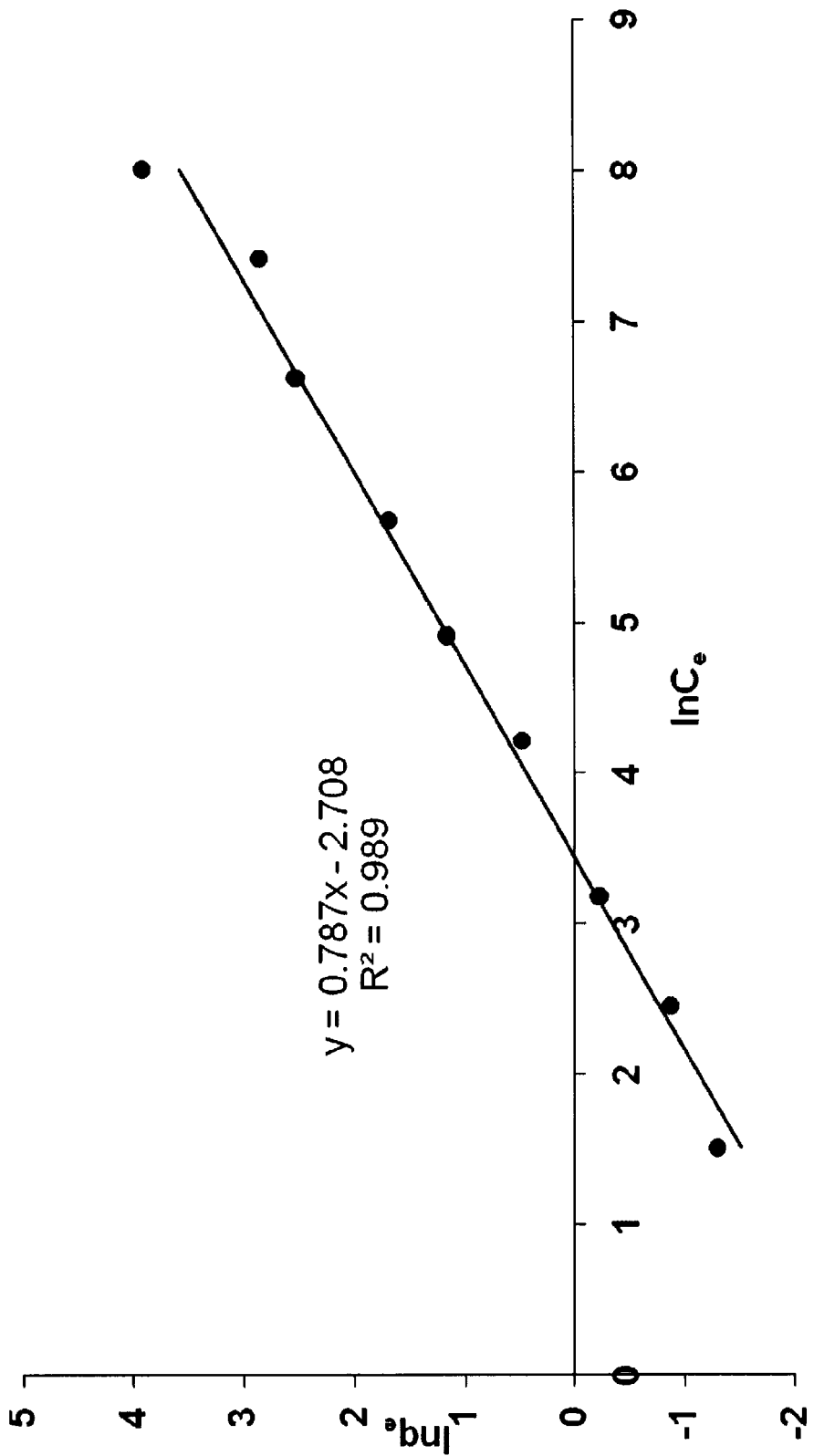
FIG. 2 shows an adsorption isotherm for blackcurrant anthocyanin extract on light blonde human hair, analysed by UV-Vis.
Figure 3:
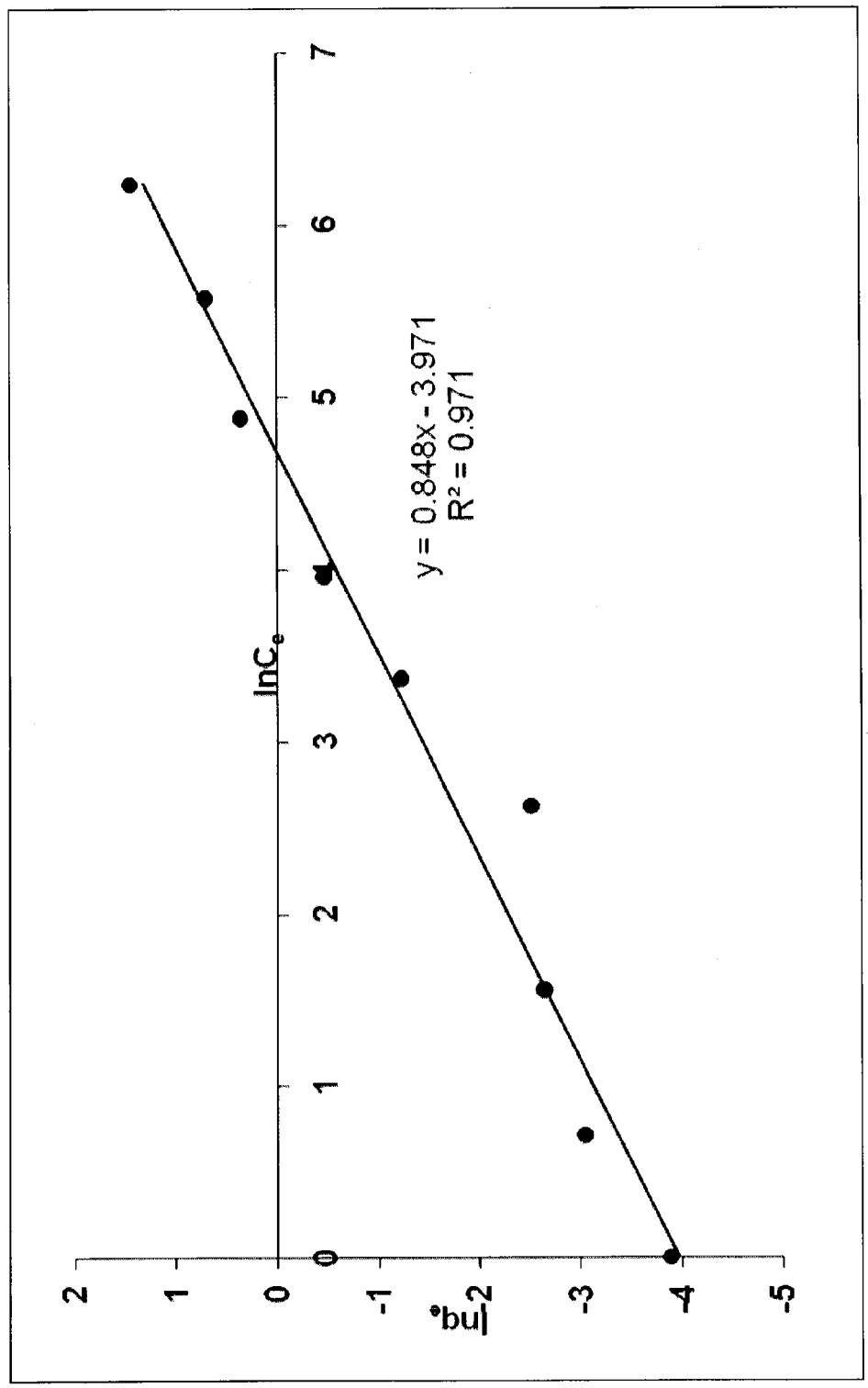
FIG. 3 Adsorption isotherm for blackcurrant anthocyanin extract on human hair, analysed by HPLC, showing total anthocyanins.

The data obtained, as set out in Table 5 above, showed a good relationship between concentration and sorption. As was expected, the lower concentration solutions gave almost complete exhaustion, with the highest concentrations showing reduced exhaustion. This data was extrapolated further, with logarithmic plots of $C_e$ (equilibrium concentration in solution, mg dm$^{-3}$) against qe (equilibrium concentration on fibre, mg g$^{-1}$). A straight-line relationship was observed from the resultant plot (as shown in FIG. 2, ln$C_e$ vs ln$q_e$, above, R2=0.990), conforming with the Freundlich isotherm description.

$$\ln q_e = \ln K_F + \frac{1}{n_F} \ln C_e \qquad \text{Equation 1}$$

The Freundlich isotherm suggests that sorption energy exponentially decreases on completion of the sorptional centres of an adsorbent, where $K_F$ is the Freundlich constant (dm$^3$ g$^{-1}$), $n_F$ is the affinity constant and 1/$n_F$ is the heterogeneity factor. Therefore, a plot of lnqe versus ln$C_e$ should yield a straight line of intercept value ln$K_F$ and slope 1/$n_F$ if the isotherm obtained through experimental observes the Freundlich expression. If $n_F$>1, then the adsorption is favourable. In the experiment described above, the intercept=−2.704, therefore $K_F$=0.066 dm$^3$ g$^{-1}$, and the gradient=0.7871, therefore $n_F$=1.27.

The adsorption study was repeated using HPLC chromatograms to assign concentrations, rather than UV-Vis absorbance. All experimental parameters were maintained, and the HPLC method was calibrated with cyanidin-3-O-glucoside chloride and cyanidin-3-O-rutinoside chloride as standards.

The results of the HPLC analysis were used to assign concentrations, rather than UV-Vis absorbance, in order to gain more accurate information regarding individual anthocyanin components of the extract.

TABLE 6

Adsorption isotherm results, measured by HPLC, for total anthocyanins

| Entry | *omf % | $C_0$ mg dm$^{-3}$ | Exhaustion % | $C_e$ mg dm$^{-3}$ | $q_e$ mg g$^{-1}$ |
|---|---|---|---|---|---|
| 1 | 20.0 | 4000 | 14.4 | 509.3 | 4.28 |
| 2 | 10.0 | 2000 | 13.3 | 264.1 | 2.03 |
| 3 | 5.0 | 1000 | 17.8 | 131.8 | 1.43 |
| 4 | 2.0 | 400 | 19.5 | 52.4 | 0.63 |
| 5 | 1.0 | 200 | 17.1 | 29.0 | 0.30 |
| 6 | 0.5 | 100 | 10.6 | 13.8 | 0.08 |
| 7 | 0.2 | 40 | 23.2 | 4.8 | 0.07 |
| 8 | 0.1 | 20 | 32.0 | 2.0 | 0.05 |
| 9 | 0.05 | 10 | 29.2 | 1.0 | 0.02 |

When Equation 1 was applied to this set of data, considering the total anthocyanin composition, again an excellent straight-line relationship was observed (R$^2$=0.972). The intercept=−3.9713, therefore $K_F$=0.019 dm$^3$ g$^{-1}$, and the gradient=0.8487, therefore $n_F$=1.17. This $n_F$ value is in good agreement with the result obtained from the initial UV-Vis monitored experiment, described above ($n_F$=1.27).

This data set was analysed based on the total anthocyanin content detected by HPLC (calibrated area under peaks). However, each peak in the chromatogram was fully resolved and characterised as the individual anthocyanin components by use of standards and confirmed by the literature. Therefore, the data set was analysed further for consideration of individual anthocyanin components (Table 7, below).

TABLE 7

Adsorption isotherm results, measured by HPLC, for two of the individual anthocyanins, where reference standards were available

| Cy-3-Glu | | | Cy-3-Rut | | |
| --- | --- | --- | --- | --- | --- |
| Ex % | $C_e$ | $q_e$ | Ex % | $C_e$ | $q_e$ |
| 20.1 | 62.3 | 0.78 | 12.2 | 171.6 | 1.20 |
| 20.0 | 32.4 | 0.40 | 10.8 | 88.8 | 0.54 |
| 22.9 | 16.5 | 0.25 | 15.8 | 44.2 | 0.42 |
| 25.4 | 6.5 | 0.11 | 16.7 | 17.6 | 0.18 |
| 22.7 | 3.7 | 0.05 | 14.2 | 9.6 | 0.08 |
| 19.7 | 1.7 | 0.02 | — | — | — |
| 34.5 | 0.6 | 0.01 | 11.0 | 1.8 | 0.01 |
| 17.5 | 0.8 | 0.01 | 32.0 | 2.0 | 0.05 |
| 20.5 | 0.4 | 0.005 | 29.2 | 1.0 | 0.02 |

Operation of the Freundlich isotherm equation (Equation 1) on the data set for cyanidin-3-O-glucoside again yielded an excellent straight-line relationship ($R^2$=0.979). The intercept=−4.202, therefore $K_F$=0.015 dm$^3$ g$^{-1}$, and the gradient=0.9686, therefore $n_F$=1.03, again in good agreement with that obtained from previous calculations (total anthocyanin $n_F$=1.17).

Figure 4:
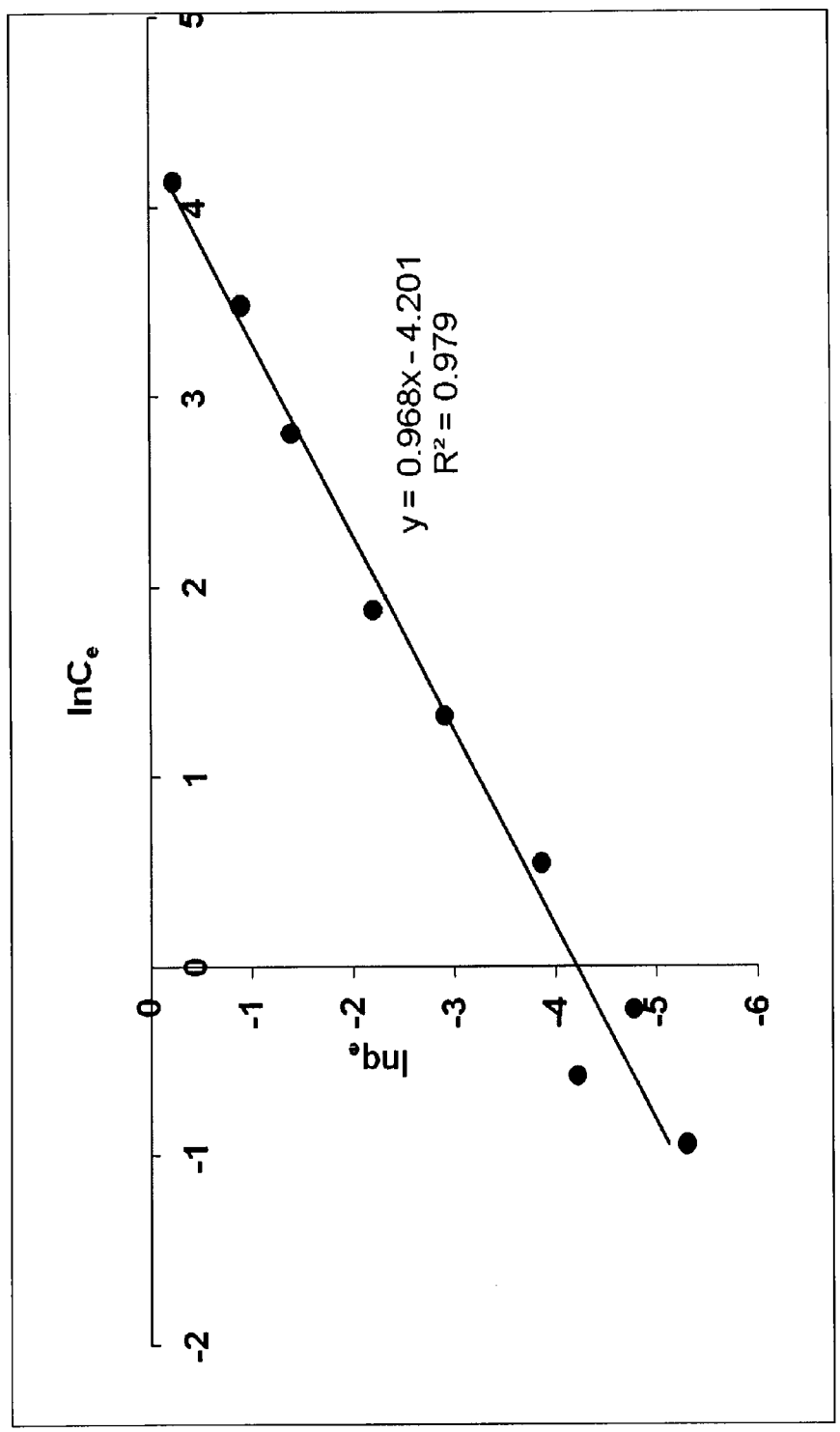
FIG. 4 shows an adsorption isotherm for cyanidin-3-O-glucoside.
Figure 5:
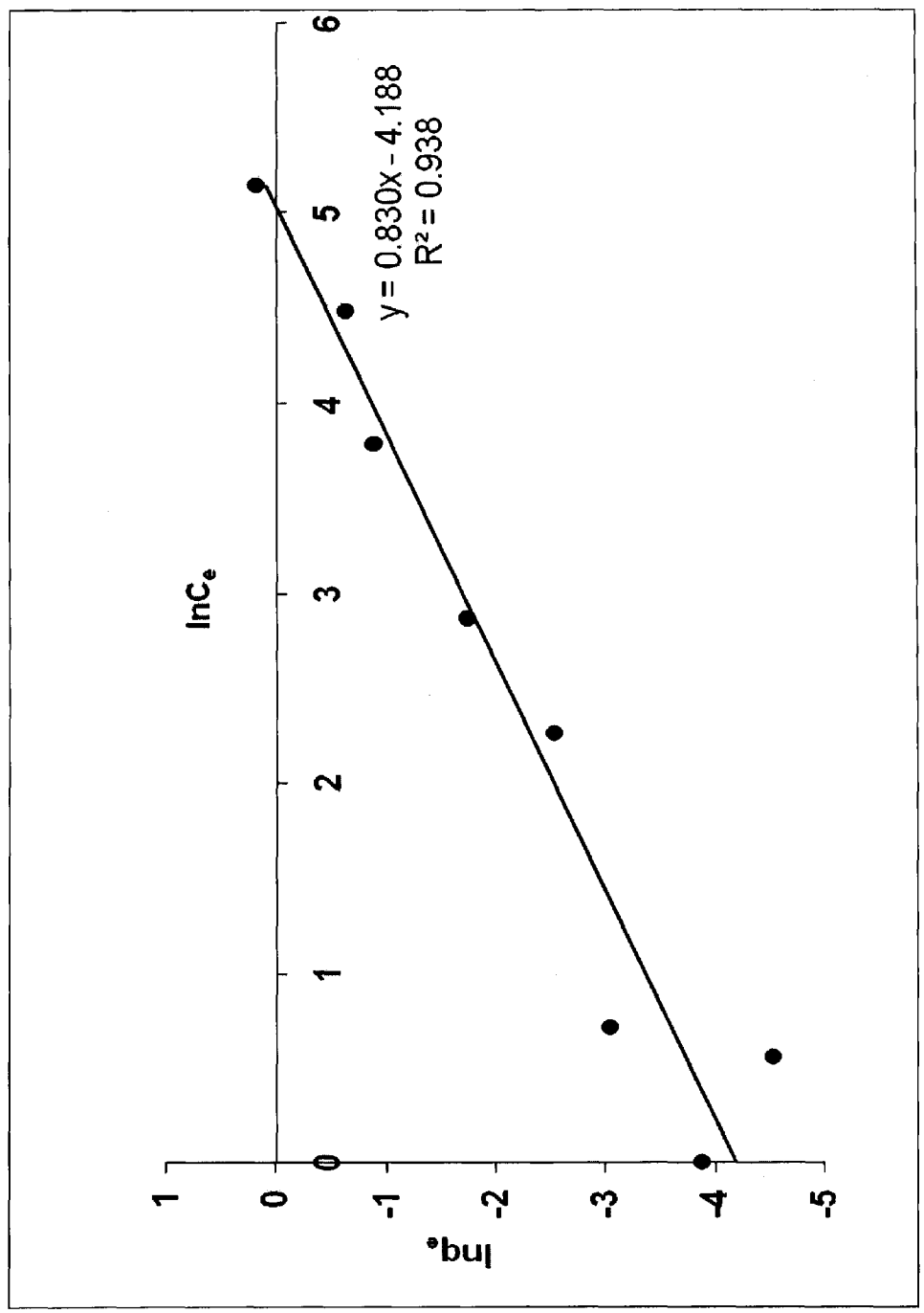
FIG. 5 shows an adsorption isotherm for cyanidin-3-O-rutinoside.

When the Freundlich equation (Equation 1) was applied to the set of data for cyanidin-3-O-rutinoside, a straight-line relationship was observed ($R^2$=0.939). The intercept=−4.1885, therefore $K_F$=0.015 dm$^3$ g$^{-1}$, and the gradient=0.8307, therefore $n_F$=1.20. This $n_F$ value is in good agreement with that obtained from consideration of the total anthocyanin content ($n_F$=1.17). These results for the contribution of individual anthocyanin components show that the adsorption is favourable for the two components shown: cyanidin-3-O-glucoside (FIG. 4) and cyanidin-3-O-rutinoside (FIG. 5).

In addition to this isotherm plot, the data may also be represented in a number of depictions in order to elucidate further information regarding the interaction between dye and fibre. One such method is to plot the logarithm of the initial dyebath concentration $\ln C_0$, versus dye on fibre, $q_e$. Such a plot allows us to understand the build up of the dye on fibre as concentration of the dyebath is increased. This plot was also necessary in order to provide a data set that could be directly compared with later colour measurement studies of hair samples dyed by colorant bases, i.e. not in aqueous solution, where pre and post dye bath concentrations could not be directly measured.

Figure 6:
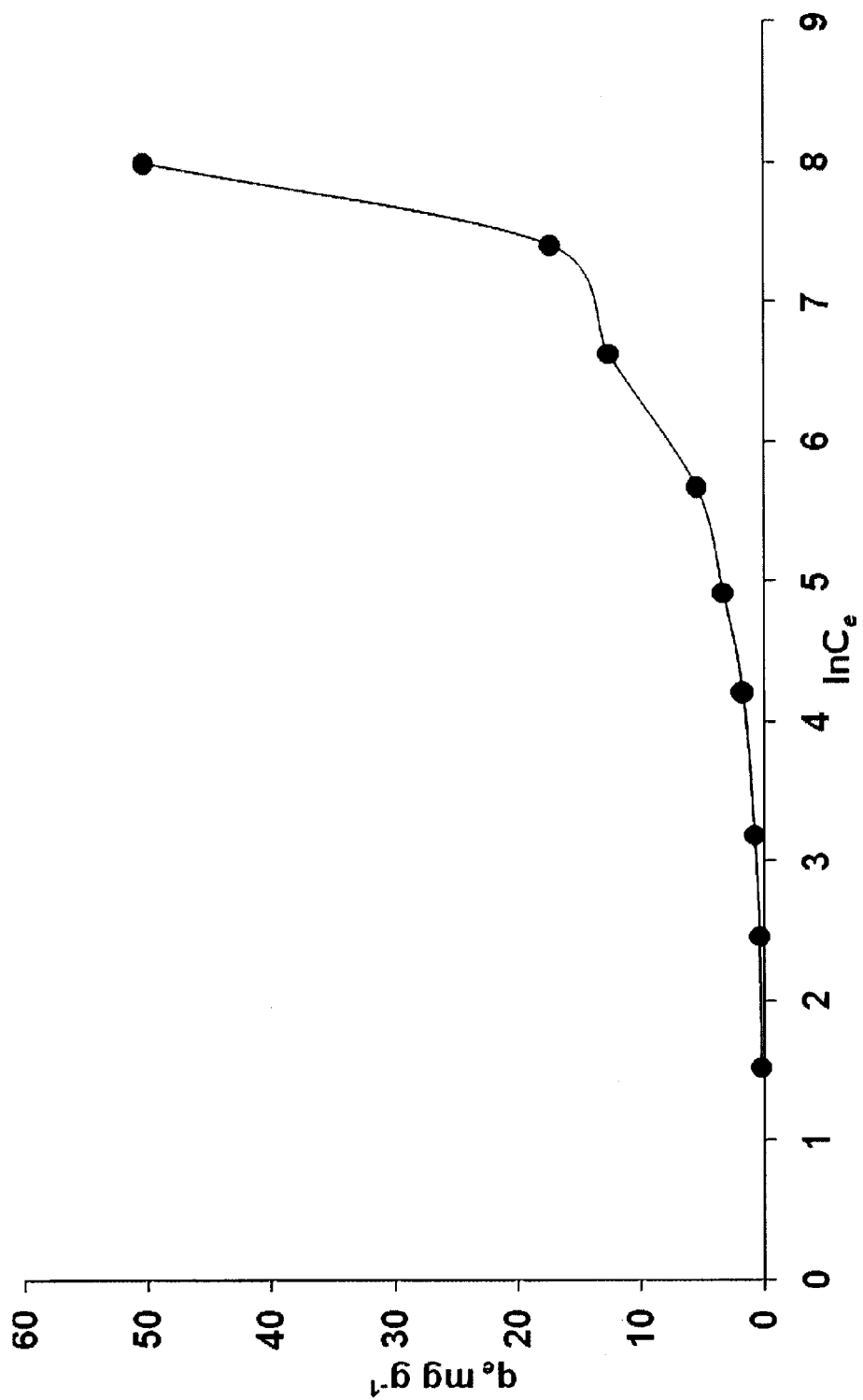
FIG. 6 shows plot for total anthocyanins of the logarithm of the equilibrium concentration $\ln C_e$, versus dye on fibre, $q_e$.

The plot in FIG. 6 exhibits a low gradient at the lowest concentrations, where 0<$\ln C_0$<4. This is consistent with a monolayer build up of dye on fibre, as expected ($q_e$<2 mg g$^{-1}$). The next portion of the plot (4<$\ln C_0$<7; 2<$q_e$<15 mg g$^{-1}$) shows an increase in gradient. It is suggested that this represents a level of sideways stacking of dye molecules (hemimicellar). Beyond this region, the gradient of the curve increases dramatically (7<$\ln C_0$<8; 15<$q_e$<50 mg g$^{-1}$). This represents multi-level stacking of the dye molecules (admicellar), effectively where colour build up occurs.

Figure 7:
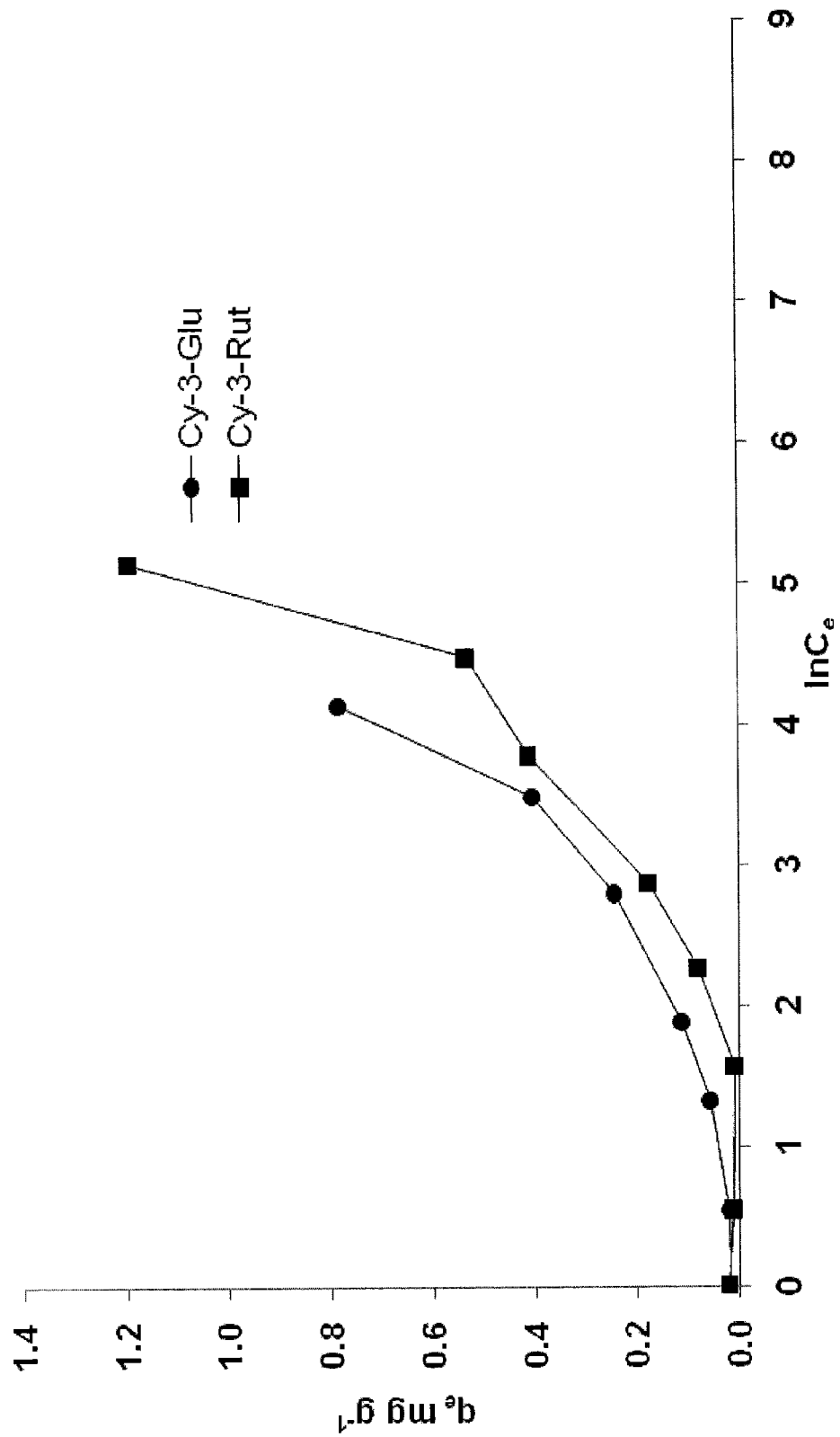
FIG. 7 shows plot for individual anthocyanins of the logarithm of equilibrium concentration $\ln C_e$, versus dye on fibre, $q_e$.

When the data was analysed for two of the individual anthocyanins, an obvious similarity in the shape of the plots was observed (as shown in FIG. 7). However, a key difference also became apparent, the values of dye on fibre ($q_e$) were higher in the case of cyanidin-3-O-glucoside than for cyanidin-3-O-rutinoside. The structural difference between these two compounds lies in the sugar substitution; cyanidin-3-O-glucoside (IV; Mw=484.84) has a monosaccharide unit whereas cyanidin-3-O-rutinoside (V; Mw=630.98) has a disaccharide unit.

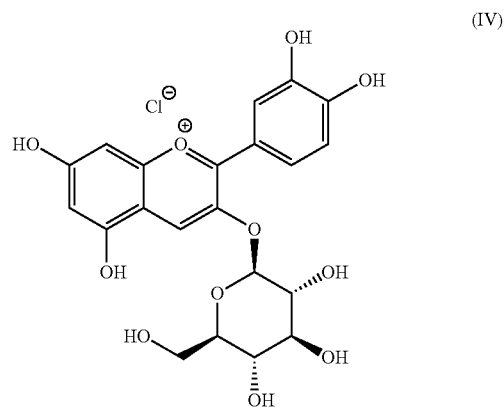

(IV)

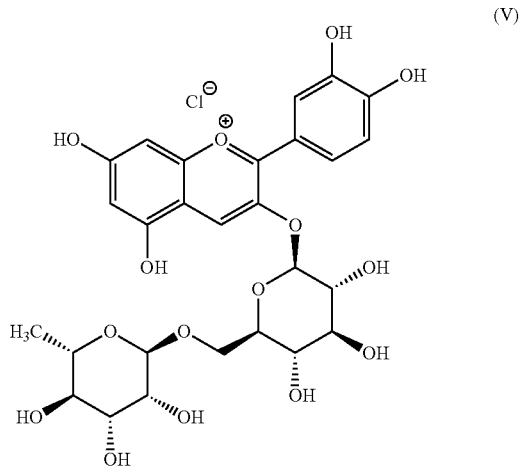

(V)

In terms of adsorption dye chemistry, this is significant where compounds of lower molecular size are favoured due to steric hindrance around sorption sites. Both the glucoside and rutinoside anthocyanins have multiple hydroxyl functional sites to facilitate hydrogen bonding with the fibre.

In conclusion, these results are consistent with the Freundlich isotherm, with hydrogen bonding and Van der Waals forces dominating the interaction between hair fibre and dye molecules.

Furthermore, these relationships were supported by colour measurement studies designed to record and quantify the change in colour of the hair fibres relative to an undyed reference sample.

Figure 8:
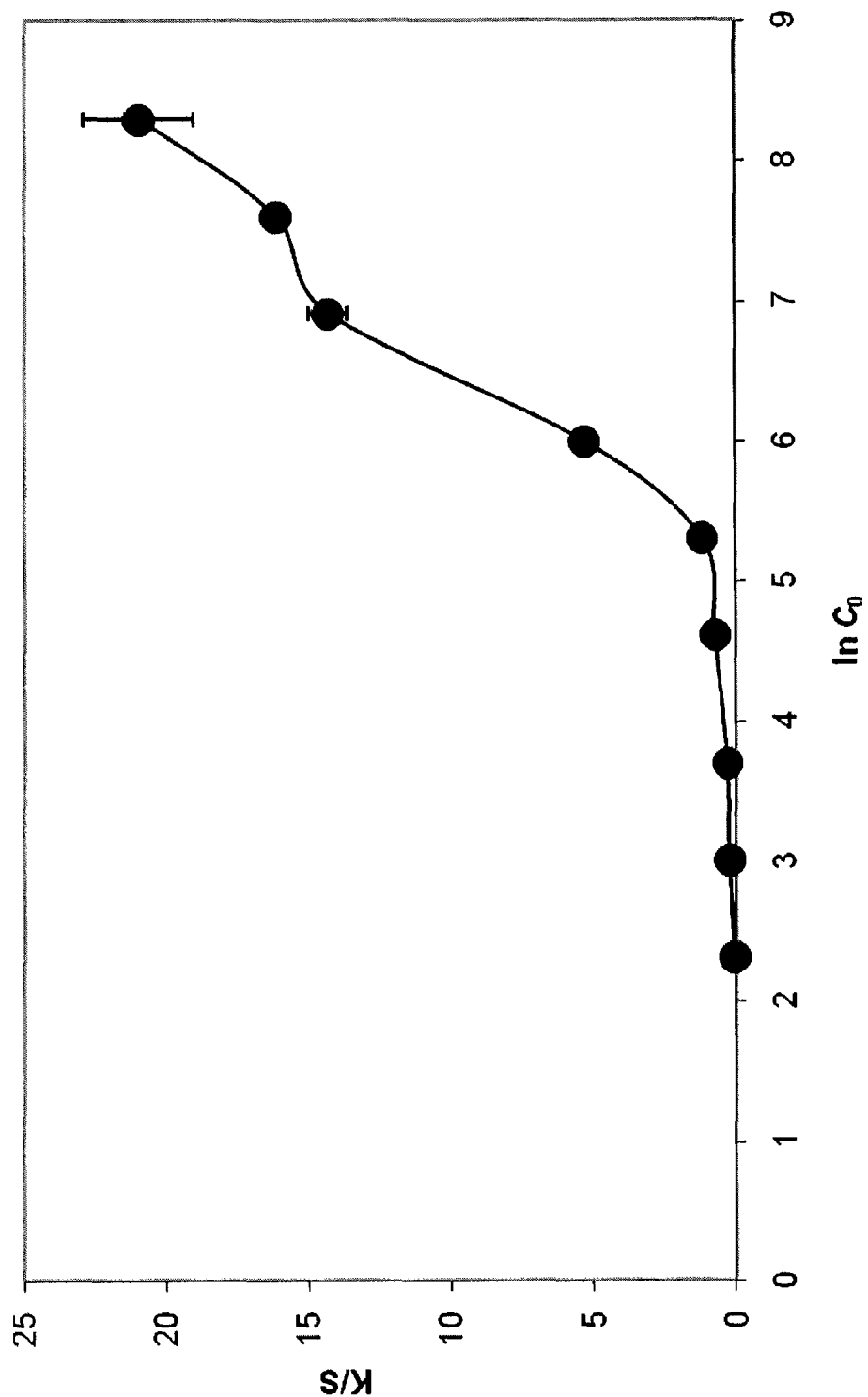
FIG. 8 shows K/S (colour strength) vs $\ln C_0$ (where $C_0$ is the initial dyebath concentration).

FIG. 8, highlights the relationship between initial dyebath concentration ($C_0$), displayed logarithmically, and the observed colour strength on hair, measured in terms of reflectance (K/S) at $\lambda_{max}$. K/S values are measured relative to a reference sample of undyed hair fibres. As can be seen, observed colour strength was very low (K/S<1) at lower data points (2<$\ln C_0$<5; K/S<1), and this was due to monolayer adsorption. At higher data points ($lnC_0>5$), a steep gradient was observed where colour strength increased noticeably ($1<K/S<22$) due to multiple-layer aggregation.

Preferential Dye Study

For further understanding of the sorption behaviour of the mixture of anthocyanins, it was necessary to investigate preferential adsorption of individual anthocyanin components. Therefore, a series of successive dyeings was performed using the same dyebath.

A sample of hair (0.40 g, light blonde, pre-shampooed) was applied to a buffered dyebath of blackcurrant anthocyanin extract (1000 mg dm$^{-3}$, 20.0 ml, 0.2 M citric acid/sodium citrate, pH 3.0). Previous studies allowed us to assume with confidence that the equilibrium of adsorption would be reached after one hour. At this point, the hair was removed from the dyebath and a second sample of hair of equal weight and pre-treatment was added. This was performed using a total of four hair samples. Although the original dyebath was calculated to have a dyebath:fibre ratio of 50:1, no additional liquid was added to compensate for minimal losses when hair fibres were removed. The validated HPLC method was used to detect anthocyanin concentration of the original dyebath, and after each successive dyeing (1 hour, RT).

Figure 9:
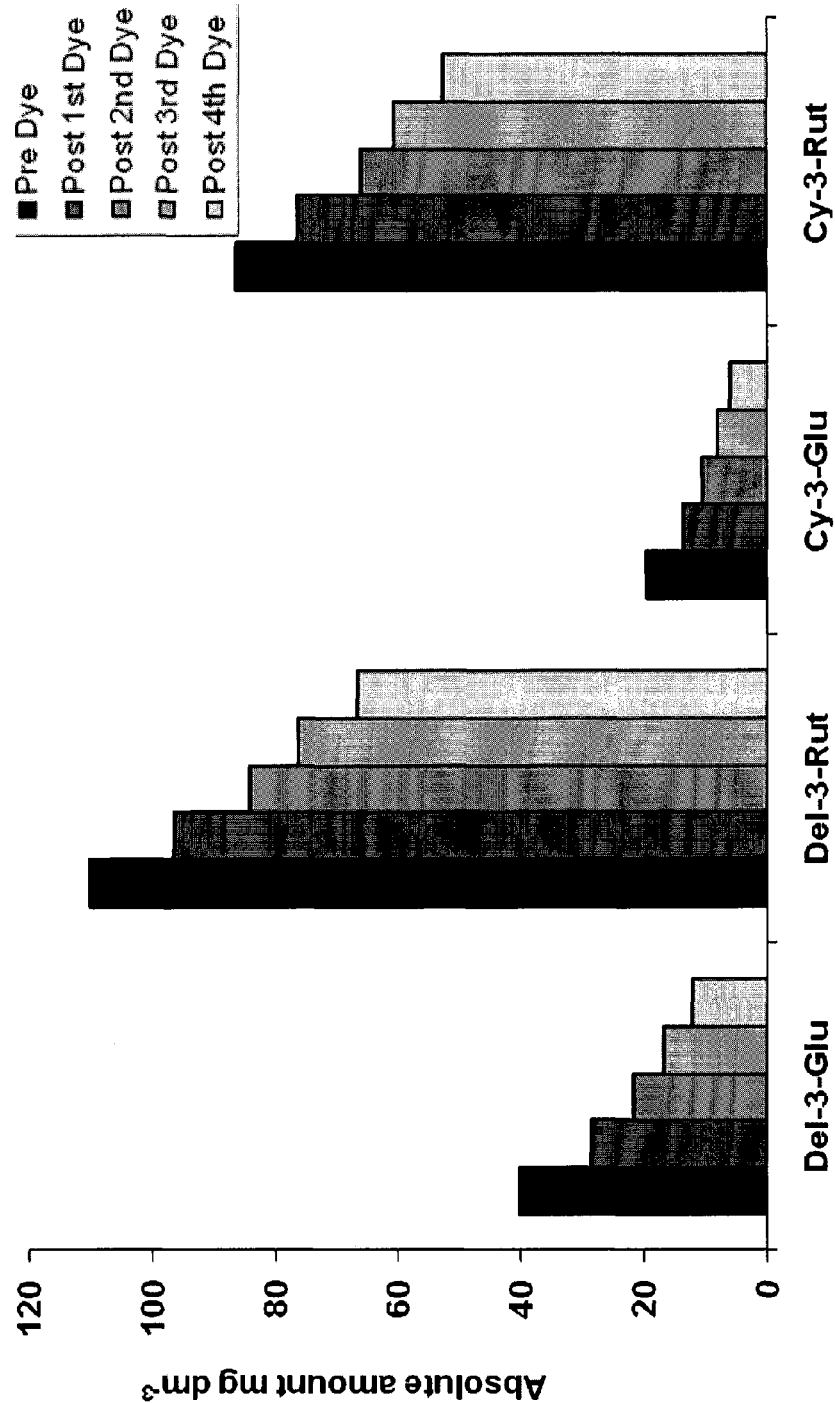
FIG. 9 shows absolute amounts of individual anthocyanins in dyebath after successive dyeings, detected by HPLC.

The data were analysed to confirm that sorption of each of the component anthocyanins was indeed favourable, and the results are set out in FIG. 9. The distribution ratio of the starting dyebath for delphinidin-3-O-glucoside: delphinidin-3-O-rutinoside: cyanidin-3-O-glucoside: cyanidin-3-O-rutinoside was found to be consistent with previous studies (15.6: 43.0: 7.6: 33.8). After the four successive dyeings, the ratio of components in the post-dye bath was found to be significantly different (8.9: 48.5: 4.2: 38.4), to suggest that the monosaccharide (glucoside) anthocyanins (Del-3-O-Glu and Cy-3-O-Glu) were preferentially adsorbed to the fibres over the disaccharide (rutinoside) anthocyanins (Del-3-O-Rut and Cy-3-O-Rut).

Figure 10:
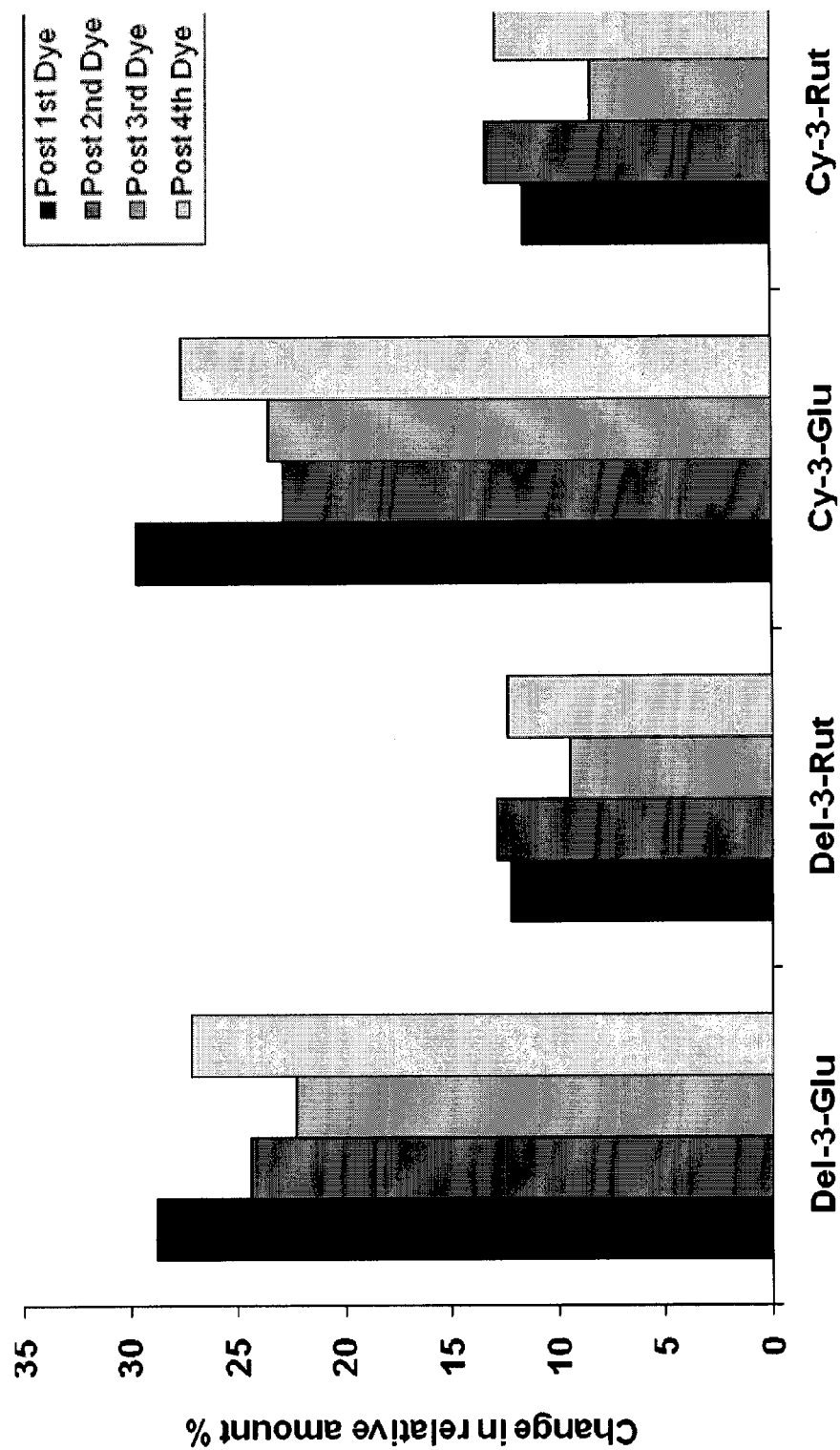
FIG. 10 shows change in relative amounts (%) of individual anthocyanins in dyebath after successive dyeings, detected by HPLC.

Change in relative amounts (%) of components was analysed further to show extremely consistent behaviour in each of the dyeings, as shown in FIG. 10. Average change in relative amounts of anthocyanins in the system was also found to be extremely consistent with respect to their sugar functionality. Both anthocyanins with monosaccharide moieties showed very similar performance (Table 8, entries 1 and 3, 25.7% and 25.9%). The statistics were also consistent in the behaviour of the pair of anthocyanins containing disaccharide units (Table 8, entries 2 and 4, 11.8% and 11.6%).

TABLE 8

Relative and average change in concentrations (%) of component anthocyanins across four successive dyeings

| Entry | Anthocyanin | Starting Relative Conc. % | Final Relative Conc. % | Average Change in Conc. % |
|---|---|---|---|---|
| 1 | Del-3-Glu | 15.6 | 8.9 | 25.7 |
| 2 | Del-3-Rut | 43.0 | 48.5 | 11.8 |
| 3 | Cy-3-Glu | 7.6 | 4.2 | 25.9 |
| 4 | Cy-3-Rut | 33.8 | 38.4 | 11.6 |

In summary, all four of the component anthocyanins were adsorbed, displaying consistent behaviour across the study, with respect to their structural and functional features. Components with smaller sugar groups were found to adsorb preferentially over those with larger sugar groups. Favourable sorption is consistent with previous isotherm studies, where hydrogen bonding was found to be the dominant interaction between anthocyanins and hair. Although the disaccharide sugar units contain more hydrogen bonding sites than monosaccharide counterparts, they also result in a larger molecular size (difference in Mw between IV and V=146.1), which is expected to hinder sorption.

Dye Base Formulation Application

Dye series were performed using two standard dye base formulations, referred herein as Base 1 (pH 5.0-5.5) and Base 2 (pH 9.0-9.5). A procedure was devised to incorporate the anthocyanin powder into each base formulation, in order to deliver the dye onto hair in a manner representative of a retail product.

The intention was to perform a comprehensive series of dyeings to allow a level of comparison with the previous aqueous systems, and to assess the general stability and behaviour of the dye within formulation. As discussed above, the primary analytical technique was reflectance colour measurement, performed on the dyed hair samples.

The dye powder (5-100 mg) was initially dissolved in the minimum solvent (~0.5 ml; 0.2 M citric acid/sodium citrate buffer, pH 3.0), and subsequently incorporated into the dye base (2.50 g), with thorough mixing. The dye paste was then applied to pre-shampooed, wetted bleached hair swatches (~1 g each), by hand with gentle massaging and combing and left to stand at room temperature for 45 minutes. After standing, the swatch was rinsed under running warm water for 2-3 minutes with combing to ensure complete removal of dye paste, subsequently conditioned and rinsed before drying with a hair dryer. Once fully dry, a reflectance colour measurement was taken of each swatch.

TABLE 9

Colour measurement (K/S) versus dye concentration.

| | | | | Base 1 | | Base 2 | |
|---|---|---|---|---|---|---|---|
| | Dye mg | | *$C_0$ | | | | |
| Entry | in 2.5 g paste | Dye wt % | mg kg$^{-1}$ | K/S | $\lambda_{max}$ | K/S | $\lambda_{max}$ |
| 1 | 5 | 0.2 | 2000 | 0.89 | 580 | 0.48 | 580 |
| 2 | 10 | 0.4 | 4000 | 1.19 | 580 | 0.98 | 580 |
| 3 | 20 | 0.8 | 8000 | 3.37 | 580 | 1.24 | 580 |
| 4 | 40 | 1.6 | 16000 | 7.20 | 580 | 3.59 | 570 |
| 5 | 100 | 4.0 | 40000 | 10.22 | 570 | 4.63 | 570 |

*$C_0$ values (mg kg$^{-1}$ paste), suggested as equivalent values to liquid phase dye baths (mg dm$^{-3}$)

Figure 11:
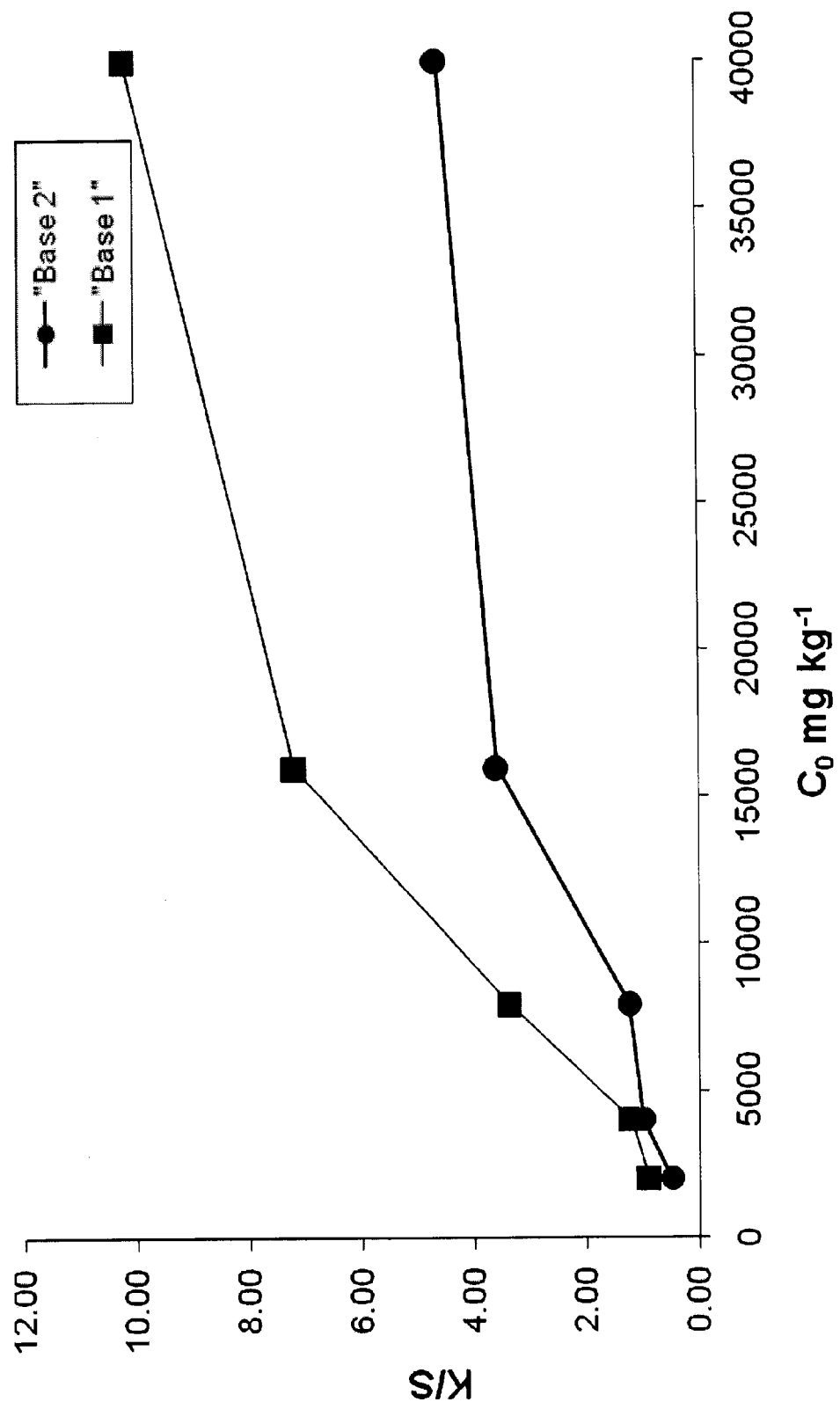
FIG. 11 shows colour measurement plot of K/S versus the logarithm of dye concentration of colorant base ($\ln C_0$) for Base 1 and Base 2 (see Table 9).
Figure 12:
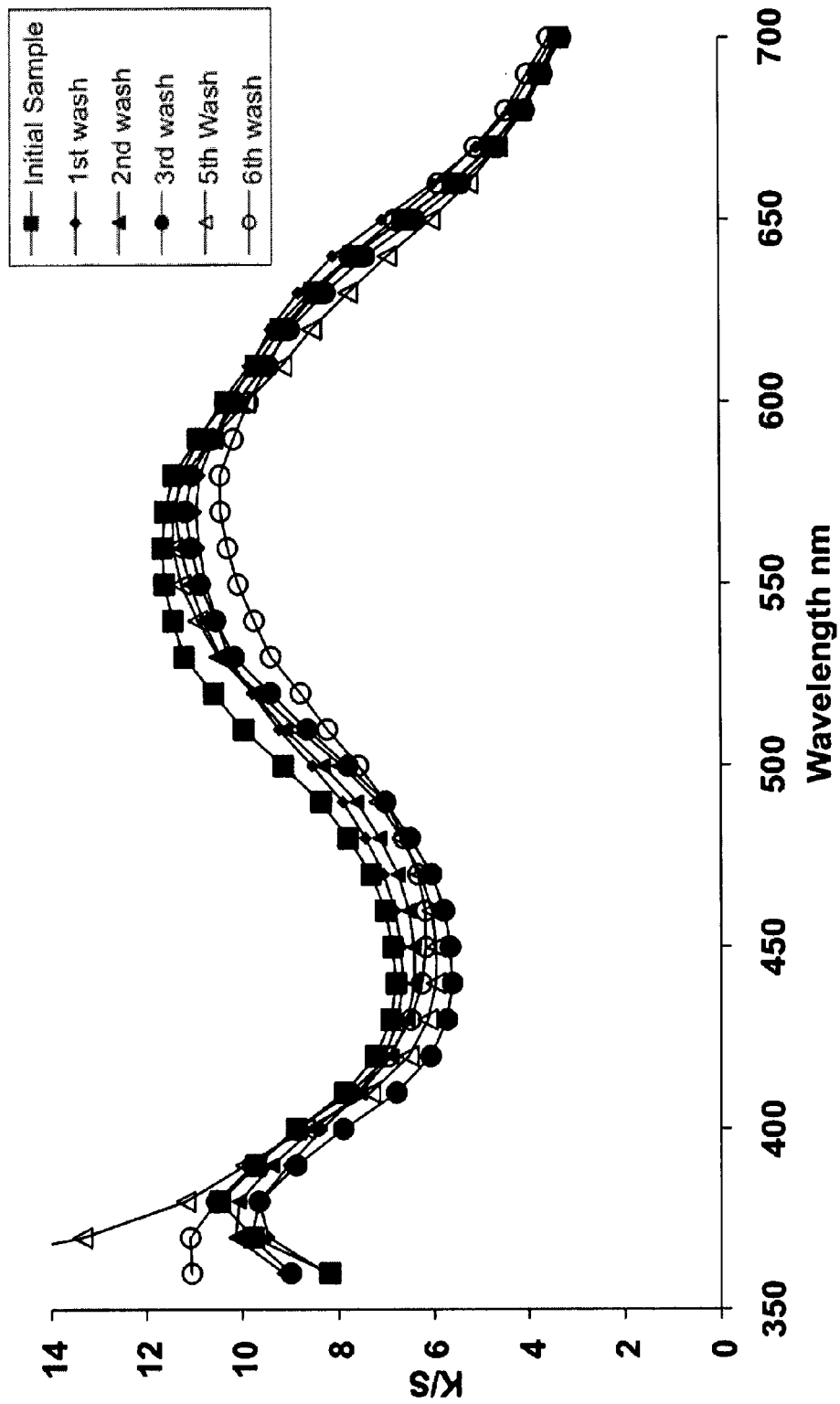
FIG. 12 shows colour measurement plot of K/S versus wavelength for wash fastness study on sample dyed with blackcurrant anthocyanins in an aqueous dyebath.

FIG. 11 highlights obvious difference between the effectiveness of the dyeings performed in the two dye bases. At low concentrations ($0.2<C_0<0.4\%$), the observed K/S values are similar. However, the lower pH base (Base 1) clearly gives superior K/S as concentration is increased, to the extent that K/S is more than twice the Base 2 value at the highest data point (4.0 wt %, K/S=10.22 vs 4.63).

Wash Fastness

Investigations into the fastness properties of the dyes to washing were performed following a standardised procedure, using shampoo and conditioner. Each wash cycle comprised of application of shampoo, thorough rinse under running warm water with combing, repeat application of shampoo, thorough rinse, followed by a single application of conditioner, final rinse, followed by drying with a domestic hair dryer with combing. A total of 6 wash cycles (12 shampoos) was conducted for each sample. Reflectance measurements (K/S) were recorded for dry hair samples after each wash cycle, where the average of 4 measurements was taken across the visible wavelength spectrum (360-700 nm).

A hair sample was dyed with blackcurrant anthocyanins in an aqueous dyebath, following our standard procedures. The initial colour intensity and absorbance maximum was recorded (FIG. 11; K/S 11.7, $\lambda_{max}$=560 nm). After the first wash cycle, as described above, minimal colour loss was observed (K/S=11.0, 6% loss), although exhibiting a shift in $\lambda$max to a higher wavelength (570 nm; note increments of 10 nm recorded). After six wash cycles the resistance to washing was found to be excellent (K/S=10.5, 10% loss), and the colour shift had stabilised ($\lambda_{max}$=570 nm).

Light Fastness

Figure 13:
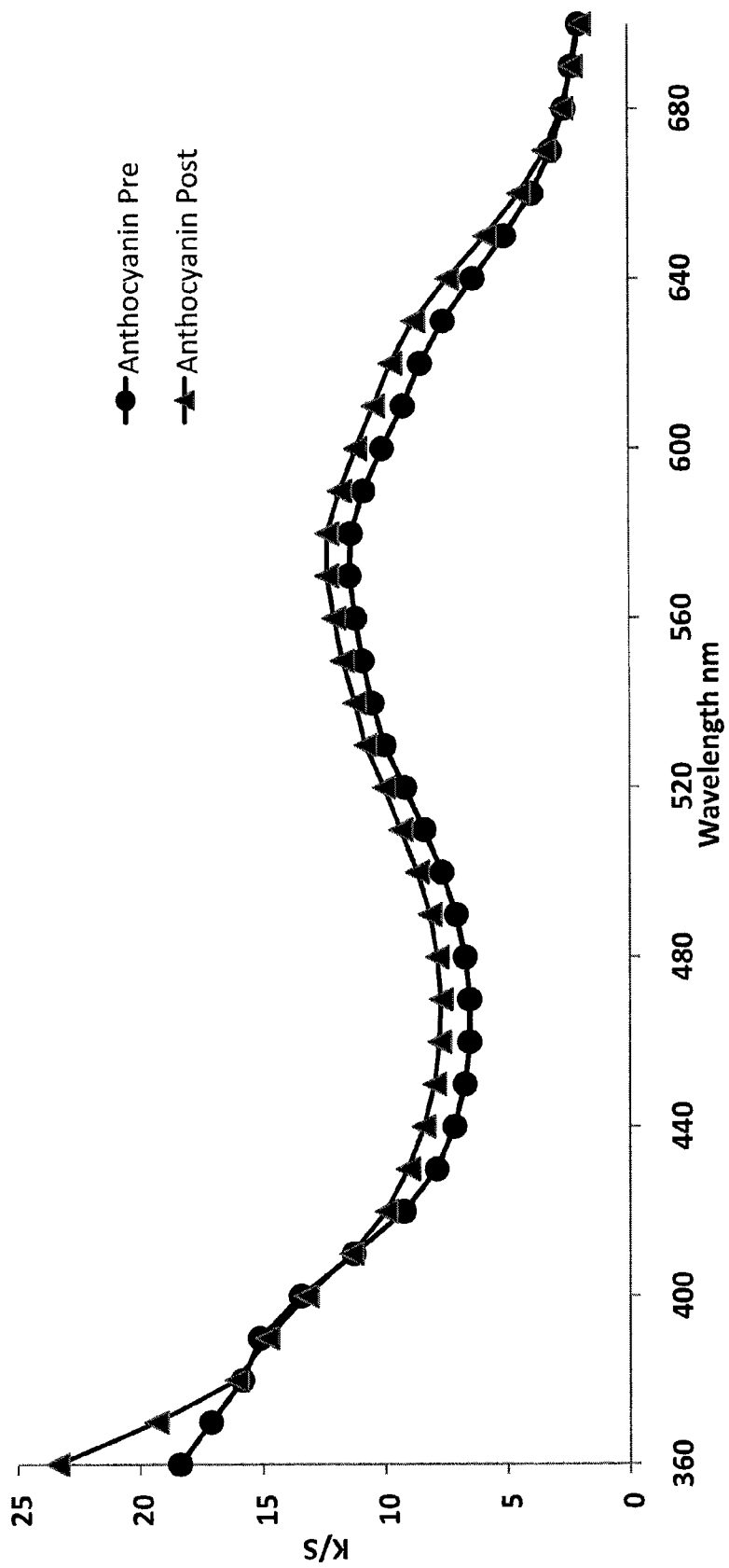
FIG. 13 shows colour measurement of hair sample dyed with blackcurrant anthocyanins in aqueous dyebath; samples taken before and after exposure to daylight simulation.
Figure 14:
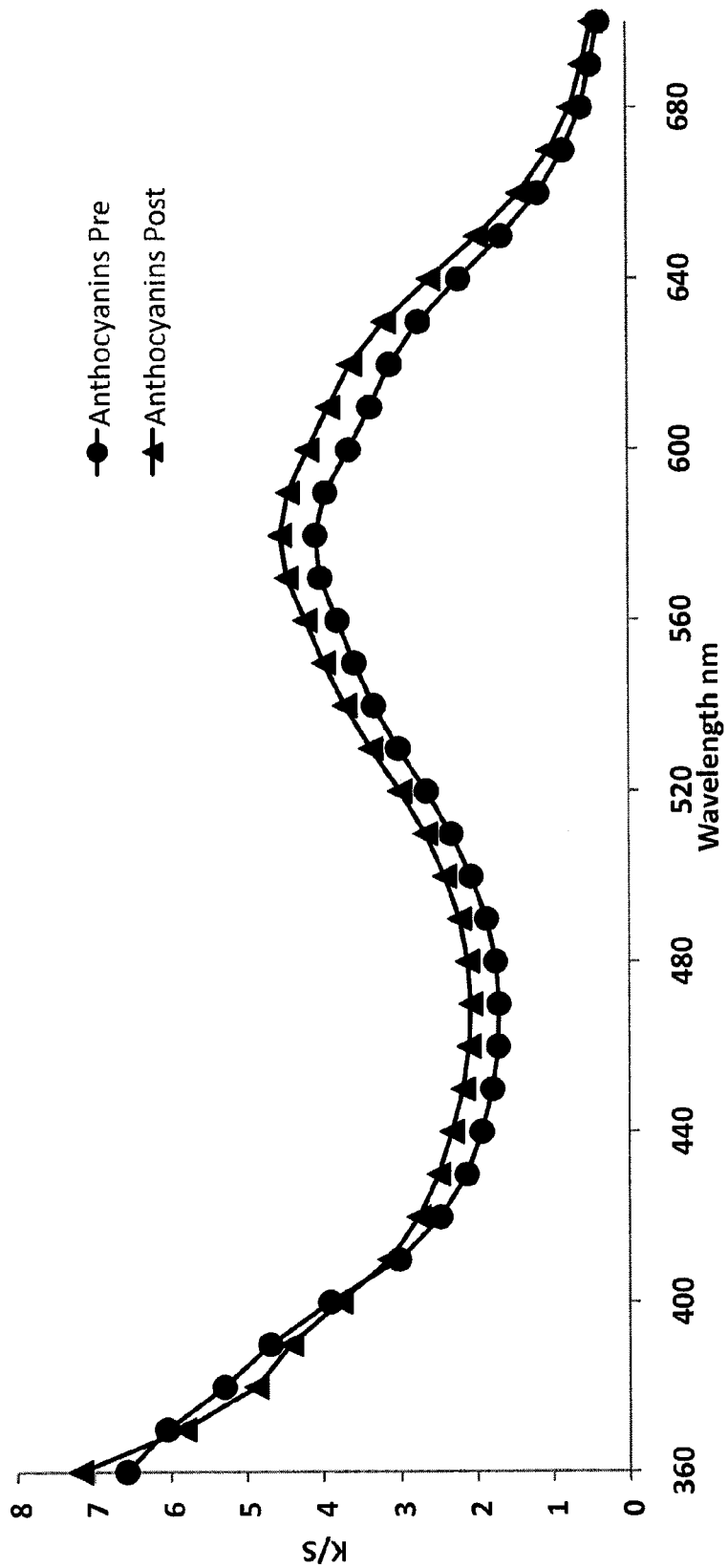
FIG. 14 shows colour measurement of hair sample dyed with blackcurrant anthocyanins in Base 1; samples taken before and after exposure to daylight simulation.

A known issue with traditional natural dyes on textile fibres is their poor fastness environmental conditions compared to modern synthetic dyes, resulting in fading upon continued exposure, for example to direct sunlight. Studies were performed using a daylight simulation lamp at controlled humidity (Atlas Xenotest Alpha LM; 60% humidity). Samples of hair dyed with anthocyanins, (in aqueous dyebaths and typical formulation bases) were run against the Blue Wool Standard, commonly used for investigations on textile dyes. The samples were all mounted within the apparatus and continuously exposed to the lamp for 6 hours. Samples were run in duplicate with additional original samples retained for reference. This was equivalent to 3.5 on the Blue Wool Standard scale. The results of the study are best displayed by comparison of the colour reflectance measurement (K/S) of samples before and after exposure (see FIGS. 13 and 14, Table 10). Colour fading would result in a reduction in the K/S value (reflectance colour intensity), and potential change in the absorption maxima ($\lambda_{max}$).

TABLE 10

Colour measurement results (K/S) and absorption maxima ($\lambda_{max}$) for samples before and after exposure to daylight simulation

| Sample | Anthocyanins $\lambda_{max}$ (nm) | K/S |
|---|---|---|
| Aqueous Pre | 570-580 | 11.5 |
| Aqueous Post | 570-580 | 12.4 |
| Base 1 Pre | 580 | 4.3 |
| Base 1 Post | 580 | 4.8 |

In the aqueous dyebath systems, the results obtained for anthocyanins showed that no discernable colour fading had occurred. In fact, the K/S values had increased slightly, which was confirmed by inspection of duplicate results, however, these are considered to be within experimental error of the technique.

These observations were repeated when the samples dyed by anthocyanins in formulation bases were inspected, including the slight increase of the K/S value. In brief summary, the hair samples dyed with anthocyanins, in either aqueous dyebaths or via formulation bases, showed excellent resistance to light exposure.

General Conditions of Application

Aspects of the invention include formulations for the treatment of human hair which comprise at least one dye mixture according to the first aspect of the invention, the use of the said dye mixtures and formulations for the dyeing of keratinous fibres which preferably comprise human hair, and methods for the semi-permanent coloration of human hair which comprise treating human hair with the said dye mixtures and formulations.

Thus, the invention comprises a method for application of anthocyanins to human hair, compatible with common cosmetic applications for coloration. The anthocyanins may be incorporated into a base formulation such as a conditioner, shampoo, or other similar product. The anthocyanins are first taken into liquid solution in any of water, ethanol, glycerol or other similar solvent. Said solvent may be modified with additives, to control pH (between 2 and 7), such as acids (e.g. hydrochloric, hydrobromic, hydroiodic, nitric, phosphoric, sulphuric, acetic, trifluoroacetic, ascorbic, citric, formic, lactic, tartaric, camphor-10-sulphonic or oxalic acids) or acidic buffer systems (e.g. citric acid/sodium citrate or other common systems) to maintain a pH between 2 and 7, at a temperature between 20 and 45° C. The anthocyanin solution is then incorporated into the appropriate delivery base formulation by mixing, at a temperature between 20 and 45° C., and at a concentration between 0.1 and 50 g anthocyanins per kg of formulation base.

The dye formulation may be then applied to human hair at a temperature between 15 and 40° C. (preferably room temperature), by hand with gentle massaging and combing as per common practice for even distribution and application of colorant pastes. The paste is then left on hair for a period of 5 to 45 minutes, whilst dye uptake onto hair takes place. The dyeing process is then ceased by thorough rinsing of the hair with water, to remove the paste. The hair may then be either conditioned, or washed with shampoo then conditioned, as would be performed in a domestic environment, to remove any residual paste and/or colorant. The hair may then be either towel dried or dried using a conventional domestic hair drier, as per usual domestic use.

Example systems and concentrations are outlined in Table 3 with their resultant reflectance colour intensity, described in K/S at the absorption maxima, when applied to light blonde human hair swatches.

The above procedure may be used as described for anthocyanin colorants, or also in conjunction with other natural compounds. When anthocyanins are used in this system as the sole or primary colorant, it is possible to achieve two effects of use to the cosmetic hair coloration industry. The first is a blue coloration of human hair, characterised by an absorption maximum in the reflectance spectrum of between 570 and 600 nm. For this effect, a concentration between 0.2 and 10 wt % of the formulations recommended. This blue coloration may therefore act as a colour component in a mixed palette to allow browns. In such a product, concentrations between 0.2 and 10 wt % of the formulations are recommended.

The second identified application is in lower concentrations to achieve a "silverising" effect. The colorant can be added to appropriate formulations such as shampoo type bases for daily application as a colour maintenance product, for example in "blonde protection" products. For this effect, concentrations between 0.01 and 0.4 wt % are most preferable.

It is known that anthocyanins in acidic aqueous solution (1<pH<4) yield a red/orange colour (500 nm <$\lambda_{max}$<530 nm; Table 11), the chromophore arising from the stable flavylium ion form (VI). When the pH of such an acidic solution is increased (4<pH<6), the purple/blue anhydrobase (VII and VIII) predominates (570 nm <$\lambda_{max}$<620 nm). However, in aqueous solution, this form is readily susceptible to hydration, resulting in the colourless pseudo-base form (IX).

TABLE 11

Figure 15:
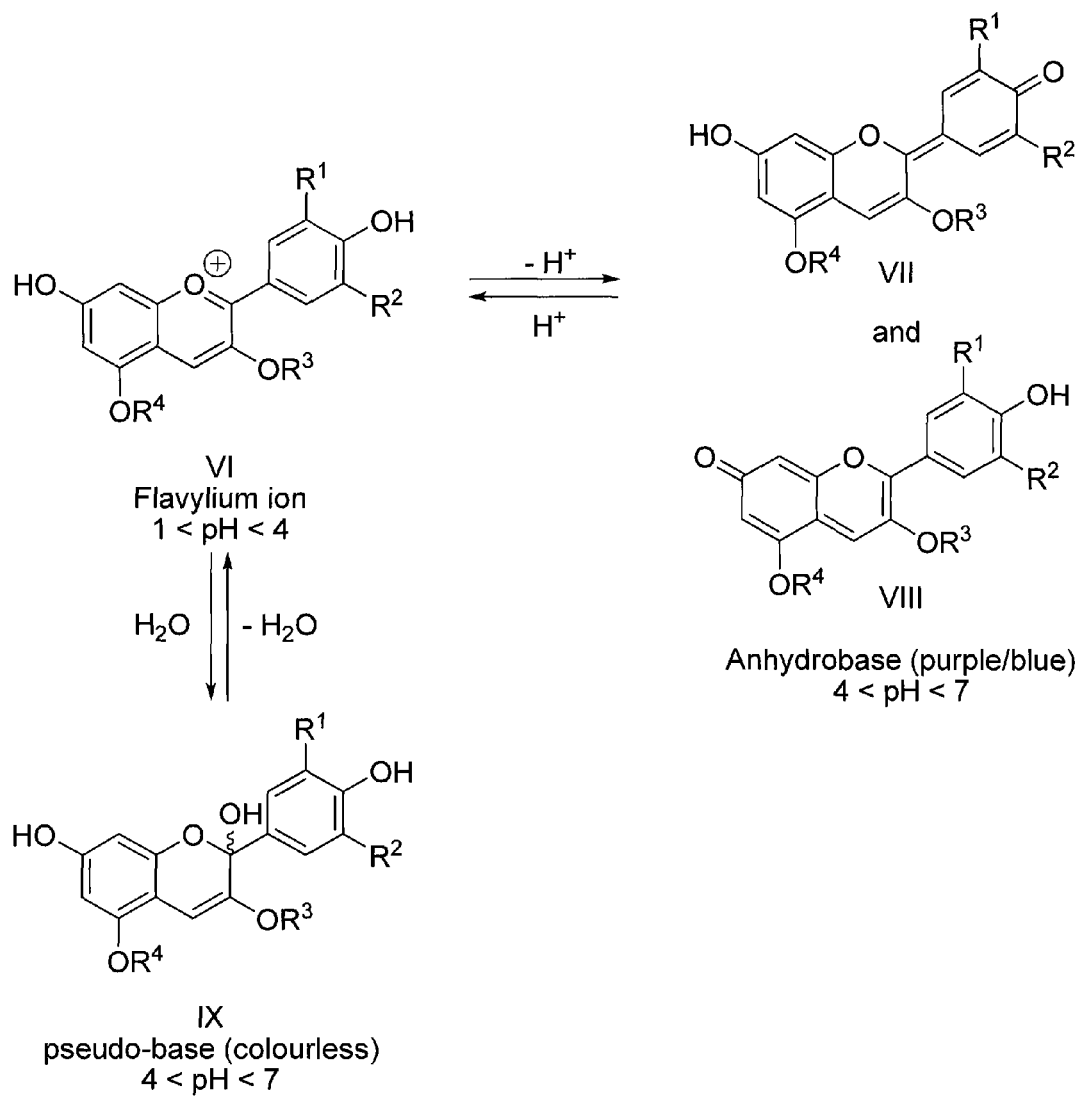
FIG. 15 shows the effect of pH change on structures of anthocyanins

Structures and absorption maxima for common anthocyanins (see also Figure 15):

| Name | R$^1$ | R$^2$ | R$^3$ | R$^4$ | *$\lambda_{max}$ |
|---|---|---|---|---|---|
| Pelargonidin | H | H | Glu | H | 503 |
| Cyanidin | OH | H | Glu | H | 517 |

TABLE 11-continued

Structures and absorption maxima for common anthocyanins (see also Figure 15):

| Name | R¹ | R² | R³ | R⁴ | *$\lambda_{max}$ |
|---|---|---|---|---|---|
| Peonidin | OCH3 | H | Glu | H | 517 |
| Delphinidin | OH | OH | Glu | H | 526 |
| Petunidin | OH | OCH3 | O-Glu | H | 526 |
| Malvinidin | OCH3 | OCH3 | O-Glu | H | 529 |

*$\lambda_{max}$ values shown are for corresponding 3-O-glucoside anthocyanins at pH 3.0

Importantly, when used for dyeing in formulation or aqueous solution at pH<4, the anthocyanins absorb onto keratin fibres (human hair) producing a blue colour consistent with the neutral anhydrobase form rather than the flavylium cation. Such an effect is unexpected and particularly relevant due to the lack of availability of natural blue dyes. It is likely that this effect is due to in situ neutralization of the cationic flavylium cation by basic sites on the hair surface leading to formation of the anhydrobase, which is again particularly notable.

Significantly, such dyed hair was also proven to be stable to wash cycles (shampoo and conditioner) and to daylight simulation. It is noted also that the actual $\lambda_{max}$ observed on hair is dependent upon the particular anthocyanins employed.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A dye mixture for application to human hair, wherein said mixture comprises a multiplicity of polyphenolic materials, wherein said materials are obtained from a botanical source, wherein said botanical source is optionally fruit, which is optionally selected from blackcurrants, blackberries, blueberries, bilberries, cranberries, grapes, chokeberries, Saskatoon berries, sea-buckthorn, mulberries acai, cherries and/or figs, wherein said polyphenolic mateials comprise glycosylated anthocyanins of the formula (III):

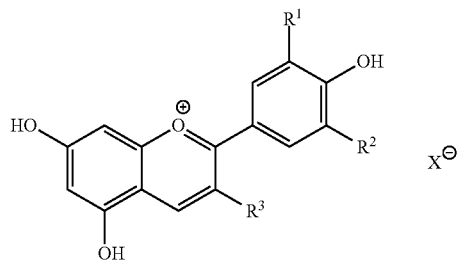

wherein R¹ and R² are, independently, H, OH or OCH₃, R³ is an O-glycosyl group (glycosylated anthocyanins), and X is a counter-ion which may optionally be selected from chloride, bromide, iodide, sulphate, bisulphate, carbonate, bicarbonate, citrate, formate, acetate or tartrate and wherein said glycosylated group comprises a monosaccharide or polysaccharide, wherein said polysaccharide optionally comprises a disaccharide or trisaccharide.

2. The dye mixture as claimed in claim 1 wherein said monosaccharide is selected from O-glucoside, O-rhamnoside, O-arabinoside, O-xyloside and O-galactoside.

3. The dye mixture as claimed in claim 1 wherein said disaccharide is selected from O-rutinoside, O-sophoroside and O-primeveroside.

4. A method for the preparation of a dye mixture for application to human hair, wherein said mixture comprises a multiplicity of polyphenolic materials, wherein said materials are obtained from a botanical source, wherein said botanical source is optionally fruit, which is optionally selected from blackcurrants, blackberries, blueberries, bilberries, cranberries, grapes, chokeberries, Saskatoon berries, sea-buckthorn, mulberries acai, cherries and/or figs, said method comprising the extraction of said mixture from at least one botanical source and the purification of said extracted material, wherein extraction of said dye mixture is achieved by the action of aqueous media and the application of heat.

5. The method as claimed in claim 4 wherein said aqueous media additionally comprises glycerol or ethanol and is acidified.

6. The method as claimed in claim 4 wherein said purification of said extracted material comprises adsorption/desorption techniques using porous solids and/or resins.

7. The method as claimed in claim 6 wherein said porous solids and/or resins comprise non-ionic aliphatic acrylic ester polymers, proteinaceous materials, polysaccharides, and modified variants thereof and said adsorption/desorption techniques comprising elution with an ethanolic liquid phase.

8. A formulation for the treatment of human hair which comprises a dye mixture as claimed in claim 1.

9. A method for the preparation of a formulation for the treatment of human hair wherein said formulation comprises a dye mixture comprising a multiplicity of polyphenolic materials, wherein said materials are obtained from a botanical source, wherein said botanical source is optionally fruit, which is optionally selected from blackcurrants, blackberries, blueberries, bilberries, cranberries, grapes, chokeberries, Saskatoon berries, sea-buckthorn, mulberries acai, cherries and/or figs, wherein said method comprises dissolution of anthocyanins into liquid solution using a solvent selected from water, ethanol or glycerol.

10. The method as claimed in claim 9 wherein said method comprises adjustment of the pH of said liquid solution of anthocyanins to between 2 and 7 by the addition of acids or acidic buffer systems, wherein said acid is optionally selected from hydrochloric, hydrobromic, hydroiodic, nitric, phosphoric, sulphuric, acetic, trifluoroacetic, ascorbic, citric, formic, lactic, tartaric, camphor-10-sulphonic or oxalic acids.

11. The method as claimed in claim 10 wherein said acidic buffer system is citric acid/ sodium citrate.

12. The method as claimed in claim 9 wherein said formulation is prepared at a temperature between 20 and 45° C.

13. A method for the semi-permanent coloration of human hair, said method comprising treating human hair with a formulation comprising a dye mixture comprising a multiplicity of polyphenolic materials, wherein said materials are obtained from a botanical source, wherein said botanical source is optionally fruit, which is optionally selected from blackcurrants, blackberries, blueberries, bilberries, cranberries, grapes, chokeberries, Saskatoon berries, sea-buckthorn, mulberries acai, cherries and/or figs.

14. The method as claimed in claim 13 wherein said formulation provides a blue coloration of human hair characterised by an absorption maximum in the reflectance spectrum between 570 and 600 nm.

15. The method as claimed in claim 13 wherein said formulation comprises at least one shampoo and/or at least one conditioner.

16. A method as claimed in claim 4 for the preparation of a dye mixture for application to human hair, wherein said polyphenolic materials comprise anthocyanin compounds.

17. A method as claimed in claim 16 wherein said anthocyanin compounds are aglycone anthocyanidins or glycosylated anthocyanins of the formula (III):

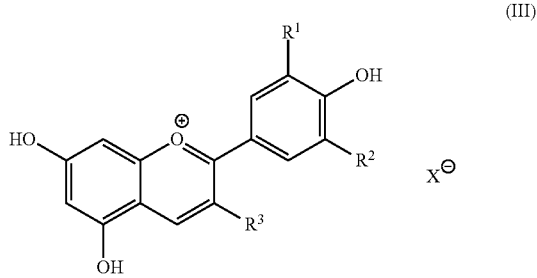

(III)

wherein $R_1$ and $R_2$ are, independently, H, OH or $OCH_3$, $R_3$ is OH (aglycone anthocyanidins) or an O-glycosyl group (glycosylated anthocyanins), and X is a counter-ion which may optionally be selected from chloride, bromide, iodide, sulphate, bisulphate, carbonate, bicarbonate, citrate, formate, acetate or tartrate.

18. A method as claimed in claim 17 wherein said at least one anthocyanin is selected from Pelargonidin (III; $R_1=R_2=H$, $R_3=OH$), Cyanidin (III; $R_1=R_3=OH$, $R_2=H$), Peonidin (III; $R_1=OCH_3$, $R_2=H$, $R_3=OH$), Delphinidin (III; $R_1=R_2=R_3=OH$), Petunidin ($R_1=R_3=OH$, $R_2=OCH_3$) and Malvinidin ($R_1=R_2=OCH_3$, $R_3=OH$).

19. A method as claimed in claim 17 wherein said glycosylated group comprises a monosaccharide or polysaccharide, wherein said polysaccharide optionally comprises a disaccharide or trisaccharide.

20. A method as claimed in claim 19 wherein said monosaccharide is selected from O-glucoside O-rhamnoside, O-arabinoside, O-xyloside and O-galactoside.

21. A method as claimed in claim 19 wherein said disaccharide is selected from O-rutinoside, O-sophoroside and O-primeveroside.

22. A method as claimed in claim 9 for the preparation of the formulation for the treatment of human hair, wherein said polyphenolic materials comprise anthocyanin compounds.

23. A method as claimed in claim 22 wherein said anthocyanin compounds are aglycone anthocyanidins or glycosylated anthocyanins of the formula (III):

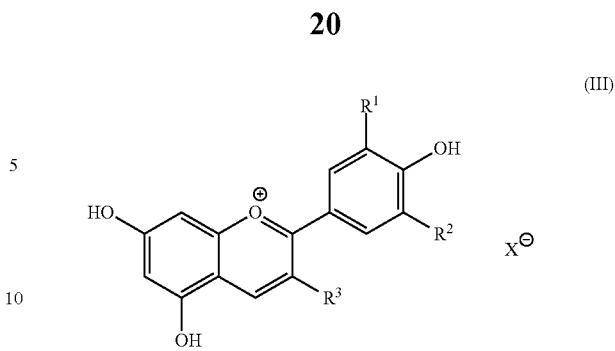

(III)

wherein $R_1$ and $R_2$ are, independently, H, OH or $OCH_3$, $R_3$ is OH (aglycone anthocyanidins) or an O-glycosyl group (glycosylated anthocyanins), and X is a counter-ion which may optionally be selected from chloride, bromide, iodide, sulphate, bisulphate, carbonate, bicarbonate, citrate, formate, acetate or tartrate.

24. A method as claimed in claim 23 wherein said at least one anthocyanin is selected from Pelargonidin (III; $R_1=R_2=H$, $R_3=OH$), Cyanidin (III; $R_1=R_3=OH$, $R_2=H$), Peonidin (III; $R_1=OCH_3$, $R_2=H$, $R_3=OH$), Delphinidin (III; $R_1=R_2=R_3=OH$), Petunidin ($R_1=R_3=OH$, $R_2=OCH_3$) and Malvinidin ($R_1=R_2=OCH_3$, $R_3=OH$).

25. A method as claimed in claim 23 wherein said glycosylated group comprises a monosaccharide or polysaccharide, wherein said polysaccharide optionally comprises a disaccharide or trisaccharide.

26. A method as claimed in claim 25 wherein said monosaccharide is selected from O-glucoside, O-rhamnoside, O-arabinoside, O-xyloside and O-galactoside.

27. A method as claimed in claim 25 wherein said disaccharide is selected from O-rutinoside, O-sophoroside and O-primeveroside.

28. A method as claimed in claim 13 for the semi-permanent coloration of human hair, wherein said polyphenolic materials comprise anthocyanin compounds.

29. A method as claimed in claim 28 wherein said anthocyanin compounds are aglycone anthocyanidins or glycosylated anthocyanins of the formula (III):

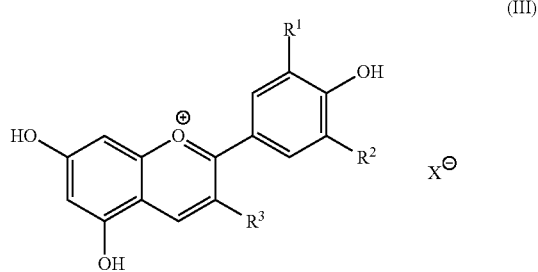

(III)

wherein $R_1$ and $R_2$ are, independently, H, OH or $OCH_3$, $R_3$ is OH (aglycone anthocyanidins) or an O-glycosyl group (glycosylated anthocyanins), and X is a counter-ion which may optionally be selected from chloride, bromide, iodide, sulphate, bisulphate, carbonate, bicarbonate, citrate, formate, acetate or tartrate.

30. A method as claimed in claim 29 wherein said at least one anthocyanin is selected from Pelargonidin (III; $R_1=R_2=H$, $R_3=OH$), Cyanidin (III; $R_1=R_3=OH$, $R_2=H$), Peonidin (III; $R_1=OCH_3$, $R_2=H$, $R_3=OH$), Delphinidin (III; $R_1=R_2=R_3=OH$), Petunidin ($R_1=R_3=OH$, $R_2=OCH_3$) and Malvinidin ($R_1=R_2=OCH_3$, $R_3=OH$).

31. A method as claimed in claim 29 wherein said glycosylated group comprises a monosaccharide or polysaccharide, wherein said polysaccharide optionally comprises a disaccharide or trisaccharide.

32. A method as claimed in claim 31 wherein said monosaccharide is selected from O-glucoside, O-rhamnoside, O-arabinoside, O-xyloside and O-galactoside.

33. A method as claimed in claim 31 wherein said disaccharide is selected from O-rutinoside, O-sophoroside and O-primeveroside.

* * * * *